US007498026B2

(12) United States Patent
Dahlqvist et al.

(10) Patent No.: US 7,498,026 B2
(45) Date of Patent: Mar. 3, 2009

(54) ACYLTRANSFERASE

(75) Inventors: Anders Dahlqvist, Furulund (SE); Alokesh Ghosal, Jadavapur (IN); Ylva Lindqvist, Jaerfaella (SE); Antoni Banas, Siedlce (PL)

(73) Assignee: Danisco US Inc., Genencor Division, Palo Alto, CA (US)

( * ) Notice: Subject to any disclaimer, the term of this patent is extended or adjusted under 35 U.S.C. 154(b) by 131 days.

(21) Appl. No.: 10/516,094

(22) PCT Filed: May 28, 2003

(86) PCT No.: PCT/SE03/00870

§ 371 (c)(1), (2), (4) Date: Nov. 24, 2004

(87) PCT Pub. No.: WO03/100044

PCT Pub. Date: Dec. 4, 2003

(65) Prior Publication Data

US 2006/0141457 A1 Jun. 29, 2006

Related U.S. Application Data

(60) Provisional application No. 60/383,889, filed on May 29, 2002.

(30) Foreign Application Priority Data

May 29, 2002 (SE) .................................... 0201581
Jan. 20, 2003 (SE) .................................... 0300142

(51) Int. Cl.
*A61K 38/45* (2006.01)
*C12N 9/10* (2006.01)
*C12Q 1/48* (2006.01)

(52) U.S. Cl. ....................... 424/94.5; 435/193; 435/810

(58) Field of Classification Search ................. 435/193, 435/810; 424/94.5
See application file for complete search history.

(56) References Cited

U.S. PATENT DOCUMENTS 4,826,767 A 5/1989 Hansen
5,324,663 A 6/1994 Lowe
5,445,947 A 8/1995 Metz et al.
6,162,623 A 12/2000 Grote et al.
6,300,487 B1 10/2001 Leung et al.

FOREIGN PATENT DOCUMENTS

JP 1320989 6/1988
WO WO 93/10241 11/1992
WO WO 97/17434 11/1996
WO 00/60095 10/2000

OTHER PUBLICATIONS

Banas et al., "Cloning and Characterisation of a Phopholipid: Diacylglycerol Acyltransferase from Arabidopsis Thaliana," (2003) *Advanced Research on Plant Lipids*, 179-182.
Brumlik et al., "Identification of the Catalytic Triad of the Lipase/Acyltransferase from Aeromonas hydrophila," (1996) *J. Bacteriol.*, 178(7):2060-2064.
Dahlqvist et al., "Phospholipid: diacylglycerol acyltransferase: An enzyme that catalyzes the acyl-CoA-independent formation of triacylglycerol in yeast and plants," (2000) PNAS 97(12):6487-6492.
Gandhi, Neena N., "Applications of Lipase," (1997) *JAOCS*, 74(6):621-634.
Jonas, Ana, "Lecithin cholesterol acyltransferase," (2000), *Biochem Biophys Acta*, 1529:245-256.
Koronelli et al., "Synthesis and Decomposition of Waxes Marine Bacteria," (1979) Vestnik Moskovskogo Universiteta. Biologiya, V34(3):62-64.

*Primary Examiner*—Tekchand Saidha

(57) ABSTRACT

The invention relates to at least one nucleotide sequence, derived from a nucleotide sequence encoding an acyltransferase polypeptide comprising at least one membrane-spanning region, encoding an improved active membrane independent acyltransferase polypeptide in which at least one amino acid residue of the membrane-spanning region has been deleted and/or substituted as compared to the original acyltransferase polypeptide, wherein the encoded active membrane independent acyltransferase polypeptide can produce fatty acid esters and/or fatty acid thioesters such as triacylglycerols, diacylglycerols, monoacylglycerols, phospholipids, glycolipids, waxesters, acylated carbohydrates, acylated amino acids, and lysolipids, e.g. lysophosphospholipid, lysolecithin. Thereby one single acyltransferase can be used for the production of a huge number of products. The invention also relates to means and methods for the production of such an improved active membrane independent acyltransferase and the use of such a membrane independent acyltransferase in industry.

17 Claims, 10 Drawing Sheets

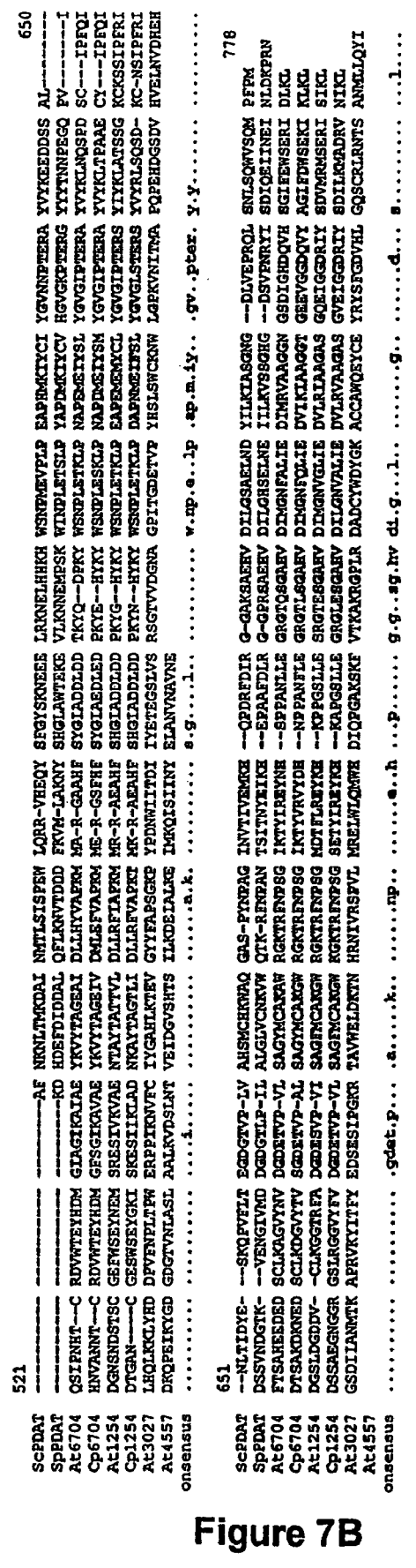

```
          521                                                                                                                                650
ScPDAT    ---------- ---------- --------AF NKNLTMKDAI NMTLSISPEW LQRR-VHEQY SFGYSKNEEE LRKNELHHKH WSNPMEVPLP EAPHMKIYCI YGVNNPTERA YVYKEEDDSS AL--------
SpPDAT    ---------- ---------- --------KD HDEFDIDDAL QFLKNVTDDD FKVM-LAKNY SHGLAWTEKE VLKNNEMPSK WINPLETSLP YAPDMKIYCV HGVGKPTERG YYYTNNPEGQ PV-------I
At6704    QSIPNHT--C RDVWTEYHDM GIAGIKAIAE YKVYTAGEAI DLLHYVAPKM MA-R-GAAHF SYGIADDLDD TKYQ--DPKY WSNPLETKLP NAPEMEIYSL YGVGIPTERA YVYKLNQSPD SC---IPFQI
Cp6704    HNVANNT--C RDVWTEYHDM GFSGIKAVAE YKVYTAGEIV DMLEFVAPKM ME-R-GSFHF SYGIAEDLED PKYE--HYKY WSNPLESKLP NAPDMEIYSM YGVGIPTERA YVYKLTPAAE CY---IPFQI
At1254    DGNSNDSTSC GEFWSEYNEM SRESIVKVAE NTAYTATTVL DLLRFIAPKM MR-R-AEAHF SHGIADDLDD PKYG--HYKY WSNPLETKLP EAPEMEMYCL YGVGIPTERS YIYKLATSSG KCKSSIPFRI
Cp1254    DTGAN----C GESWSEYGKI SKESIIKLAD NKAYTAGTLI DLLRFVAPKT MK-R-AEAHF SHGIADDLDD PKYN--HYKY WSNPLETKLP DAPNMEIFSL YGVGLSTERS YVYRLSQSD- KC-NSIPFRI
At3027    LHQLKKLYHD DPVFNPLTPW ERPPIKNVFC IYGAHLKTEV GYYFAPSGKP YPDNWIITDI IYETEGSLVS RSGTVVDGNA GPITGDETVP YHSLSWCKNW LGPKVNITMA PQPEHDGSDV HVELNVDHEH
At4557    DKQPEIKYGD GDGTVNLASL AALKVDSLNT VEIDGVSHTS ILKDEIALKE IMKQISIINY ELANVNAVNE
onsensus  .......... .......... ....i..... .......... ......a.k. .......... s.g....l.. .......... w.np.e..lp .ap.m.iy.. .gv..pter. y.y....... ..........

          651                                                                                                                             778
ScPDAT    --NLTIDYE- ---SKQPVFLT EGDGTVP-LV AHSMCHKWAQ GAS-PYNPAG INVTIVEMKH --QPDRFDIR G-GAKSAEHV DILGSAELND YILKIASGNG --DLVEPRQL SNLSQWVSQM PFPM
SpPDAT    DSSVNDGTK- --VENGIVMD DGDGTLP-IL ALGLVCNKVW QTK-RFNPAN TSITNYEIKH --EPAAFDLR G-GPRSAEHV DILGHSELNE IILKVSSGHG --DSVPNRYI SDIQEIINEI NLDKPRN
At6704    FTSAHEEDED SCLKAGVYNV DGDETVP-VL SAGYMCAKAW RGKTRFNPSG IKTYIREYNH --SPPANLLE GRGTQSGAHV DIMGNFALIE DIMRVAAGGN GSDIGHDQVH SGIFEWSERI DLKL
Cp6704    DTSAKDKNED SCLKDGVYTV SGDETVP-AL SAGYMCAKGW RGKTRFNPSG IKTYVRVYDH --NPPANFLE GRGTLSGAHV DIMGNFQLIE DVIKIAAGGT GEEVGGDQVY AGIFDWSEKI KLKL
At1254    DGSLDGDDV- -CLNGGTRFA DGDESVP-VI SAGFMCAKGW RGKTRFNPSG MDTFLREYKH --KPPGSLLE SRGTESGAHV DIMGNVGLIE DVLRIAAGAS GQEIGGDRIY SDVMRMSERI SIKL
Cp1254    DSSAEGNGGR GSLRGGVYFV DGDETVP-VL SAGFMCAKGW KGKTRFNPSG SETYIREYKH --KAPGSLLE GRGLESGAHV DILGNVALIE DVLRVAAGAS GVEIGGDRIY SDILKMADRV NIKL
At3027    GSDIIANMTK APRVKYITFY EDSESIPGKR TAVWELDKTN HRNIVRSPVL MRELWLQMWH DIQPGAKSKF VTKAKRGPLR DADCYWDYGK ACCAWQEYCE YRYSFGDVHL GQSCRLRNTS ANMLLQYI
At4557
onsensus  .......... .......... .gdet.p... .a.....k.. ......np.. ......e..h ...p...... g.g..sg.hv di.g...l.. .......g.. ......d... s......... ...l....
```

Figure 7B

ACYLTRANSFERASE

FIELD OF INVENTION

The invention relates to at least one nucleotide sequence, derived from a nucleotide sequence encoding an acyltransferase polypeptide comprising at least one membrane-spanning region, encoding an improved active membrane independent acyltransferase polypeptide in which at least one amino acid residue of the membrane-spanning region has been deleted and/or substituted as compared to the original acyltransferase polypeptide, wherein the encoded active membrane independent acyltransferase polypeptide can produce fatty acid esters and/or fatty acid thioesters such as triacylglycerols, diacylglycerols, monoacylglycerols, phospholipids, glycolipids, waxesters, acylated carbohydrates, acylated amino acids, and lysolipids, e.g. lysophosphospholipid, lysolecithin. Thereby one single acyltransferase can be used for the production of a huge number of products. The invention also relates to means and methods for the production of such an improved active membrane independent acyltransferase and the use of such a membrane independent acyltransferase in industry.

BACKGROUND OF INVENTION

A phospholipid: diacylglycerol acyltransferase (PDAT) has biochemically been characterised in yeast and plants and a gene, LRO1, encoding the PDAT enzyme was identified in yeast (Dahlqvist et al., 2000, PNAS 97:6487-6492). The enzyme was shown to catalyse the formation of triacylglycerols (TAG) by an acyltransfer from phospholipids to diacylglycerols (DAG). Furthermore, the enzymatic activity was found to be localised in the microsomal fraction. The gene encoding the PDAT enzyme was shown to have sequence homologies to the lecithin: cholesterol acyltransferase (LCAT) gene family. The LCAT enzyme is used for the treatment of LCAT deficiencies, such as arteriosclerosis by increasing the activity of LCAT in serum of the mammal to a level effective to decrease the accumulation of cholesterol (WO9717434). The diet habit used by large groups of people today result in high cholesterol values with all other problems, which follow.

Lipases are enzymes that are primarily responsible for the hydrolysis of glycerolipids such as triacylglycerols. However, it is well known that lipases also under certain conditions in water free systems, can catalyse interesterification (Gandhi, 1997, J Am Oil Chem Soc 74 (6): 621-634). The wide berth for employment in a variety of reactions and broad substrate specificity has rendered the lipases to be very useful in a variety of applications such as production of pharmaceuticals, cosmetics, detergents, foods, perfumery, and other organic synthetic materials. One example is the use of an immobilised lipase for the synthesis of waxes (U.S. Pat. No. 4,826,767 and U.S. Pat. No. 6,162,623). The low stability, low activity or selectivity encountered occasionally with a number of these enzymes have been the chief obstacle hindering a more rapid expansion of industrial lipase technology into new applications on a large scale.

Additionally, mass-production of waxes have been performed by culturing microorganisms, together with fatty-acids, wherein acyltransferases present within the microorganism convert the fatty acids into waxesters, such as by using the microorganism *Staphylococcus lentus* (JP 1320989). Another example is the use of *Arthrobacter ceroformans* for the production of waxesters (Koronelli et al., 1979, Vestn. Mosk. Univ. Ser 16, Biol 3:62-64). Other examples are the use of transgenic hosts harbouring a gene encoding an acyltransferase for the production of waxes, as described in WO 9310241 and U.S. Pat. No. 5,445,947.

Industrial application using the above mentioned lipases as biocatalyst, for the production of a variety of waxesters, is limited to the group of lipases and the restrictions these enzymes have both regarding the products that could be produced and the conditions by which these enzymes are active. For example, the esterification must occur in water free solvents and under reduced pressure.

By the use of microorganisms there are limitations such as the need of several purification steps after the synthesis of the waxesters to be able to remove the microorganism and other impurities, which comes along with the culturing method. There are also difficulties in obtaining high yields of the waxesters. The microorganism may be one that naturally encodes enzymes suitable for the synthesis of waxesters, or a genetically modified microorganism, which by the modification obtains the ability to produce waxesters.

Furthermore, the waxesters that can be synthesised today are limited due to the substrate specificity of the enzymes catalysing the wax ester synthesis in these microorganisms. Moreover, these enzymes are integral membrane enzymes, which render it impossible to use such enzymes as biocatalyst in a cell free system such as in an industrial reactor.

There is a need for new improved enzymes, which enables the production of variety of fatty acid esters to high yields in cost-efficient industrial processes. Examples of fatty acid esters are structured glycerol fatty acid esters such as triacylglycerols with a specific acyl group at the sn2 positions that differs as compared to that of the outer positions and diacylglycerols with specific acylgroups. Production of fat-soluble fatty acid esters by acylation of water-soluble molecules, such as flavours and vitamins, is another example of desirable fatty acid esters. Other valuable fatty acid esters of interest are waxesters (i.e. fatty acids esterified to long chain alcohols), or fatty acid esters of molecules such as carbohydrates and amino acids. A method for the production of such compounds can be achieved by optimising enzymes that already is used as biocatalyst exemplified by the well-known families of lipases or other membrane independent enzymes. However, in nature many of the enzymes catalysing the transfer of acylgroups are integral membrane proteins. Among the membrane independent acyltransferases present in nature the vast majority catalyses an acyl-CoA dependent reaction. Both these classes of acyltransferases are not suited as a biocatalyst in industrial methods since integral membrane protein are not functioning in cell free systems and acyl-CoA is a to costly substrate. Furthermore, in applications involving enzymes belonging to the lipase family the interesterification is dependent on a water free system. Hence, membrane independent acyltransferases that could use acyl-lipids as acyl donors in industrial methods for the manufacturing of fatty acid esters are limited today and no such enzyme is available which can manufacture several different fatty acid ester and/or fatty acid thioesters, i.e., use a lot of different acyl donors and acyl acceptors.

There are also needs for enzymes to be used to improve the properties of complex raw material. For example within the area of food production, modification of different components such as lipids present in food raw material such as milk cereals, vegetables, eggs, vegetable oils, meat, fish, etc is desirable. Examples of improvements achieved by such modifications are enhanced emulsifying properties, increased shelf life, less off-flavour, etc. For example in many food applications enhanced emulsifying properties are desirable and can be achieved by converting phospholipids (i.e. lecithin) present in the food raw material into lysophospholipids.

Lipases are commonly used in such applications resulting in elevated levels of lysophospholipids but also unesterified fatty acids that can result in off-flavours. Conversion of phospholipids into lysolipids without increased amounts of unesterified fatty acids is therefore desirable and can be achieved with acyltransferases that transfer the fatty acid from the phospholipid to an acyl acceptor such as monoacylglycerols, diacylglycerols, alcohols, or any other acyl acceptors present in or added to the raw material.

BRIEF DISCLOSURE OF THE INVENTION

Accordingly, in a first aspect the invention relates to one or more nucleotide sequence(s), derived from a nucleotide sequence encoding an acyltransferase polypeptide comprising at least one membrane-spanning region, encoding an improved active membrane independent acyltransferase polypeptide in which at least one amino acid residue of the membrane-spanning region has been deleted and/or substituted as compared to the original acyltransferase polypeptide, wherein the encoded active membrane independent acyltransferase polypeptide can produce lysolipids and fatty acid esters and/or fatty acid thioesters such as lysophosphospholipid, lysolecithin, triacylglycerols, diacylglycerols, monoacylglycerols, phospholipids, glycolipids, waxesters, acylated carbohydrates and acylated amino acids. Such an improved acyltransferase can be used in a huge number of chemical reactions for the production of a large number of different fatty acid esters and/or fatty acid thioesters, which enables the possibility to in a economic way produce a large amount of a single enzyme which then can be used for several purposes.

Additionally, such an acyltransferase, which is capable of catalysing several reactions, enables the possibility to facilitate the production of a number of fatty acid esters and/or fatty acid thioesters by one single acyltransferase. Such an active membrane independent acyltransferase polypeptide may be used in a bioreactor for the production of desired fatty acid esters or as additive in food raw material for modification of its lipid composition without the need of a microorganism or a lipid membrane for the maintenance of the acyltransferase activity.

In another aspect, the invention relates to a nucleotide sequence molecule comprising at least one promoter region which functions in a host, the promoter region is operably linked to at least one nucleotide sequence as described above, which is operably linked to at least one non-translated region which functions in a host.

In a further aspect, the invention relates to a method for the production of an active membrane independent acyltransferase polypeptide comprising the steps of providing a host cell and a growth medium preparing a host cell culture, culturing the host cell culture and harvesting the host cell culture and recovering the polypeptide.

By providing a nucleotide sequence encoding a membrane independent acyltransferase without the ability to become integrated into a membrane and having the ability to utilise different acyl donors and acyl acceptors, the ability to manufacture acylated products by a sole enzyme (i.e. fatty acid esters) is increased.

The membrane independent acyltransferase may be used in applications such as cosmetics, pharmaceuticals, foods, food additives, candles, soaps, detergents, laundries, polymers, coatings, plasticizer, drying oils, lubricants, varnishes, linoleum, printing, inks, textile dyes and surfactants, especially within the area of synthesis of stereo specific isomers, which not is possible with the use of conventional organic synthesis.

Furthermore, the synthesis of fatty acid esters with the use of such an enzyme in a cell free method, such as in a bioreactor can be more efficient and less restricted since the method is only limited to the conditions by which the enzyme is active, whereas in a fermentation method the limitations is set by the conditions for the maintenance of the microorganisms. In such a fermentation system the fatty acid ester products to be synthesised is limited to the building components, such as acyl donors and acyl acceptors present within the cell, whereas in a cell free system the limitation is only set by the properties of the enzyme such as substrate specificity. In a cell free system it is easy to calculate the amounts of the building components which are necessary to add to obtain an optimised enzyme catalysed method in which most of the building components ends up in the desired products such as fatty acid esters. Moreover, the use of lipases in a method for the synthesis of fatty acid esters is limited to water free conditions whereas membrane independent acyltransferases catalyses the acyl transfers in water containing systems.

Furthermore, use of a membrane independent acyltransferase as compared to a microorganism for the synthesis of for example lysophospholipids and/or fatty acid esters reduces the need of removing the microorganism after the synthesis is finalised By the use of the new improved enzyme according to the invention it is possible to produce structured lipids without the need of organic solvents, which would be both environmentally favourable, healthier and eliminates one or more purification steps after the production of the structured lipids. Additionally, it may be easier to get an approval by the authorities for such a product, manufactured in a process without the use of organic solvents.

DESCRIPTION OF THE DRAWINGS

The invention is illustrated with reference to the drawings in which.

DETAILED DESCRIPTION OF THE INVENTION

Definitions

Figure 1:
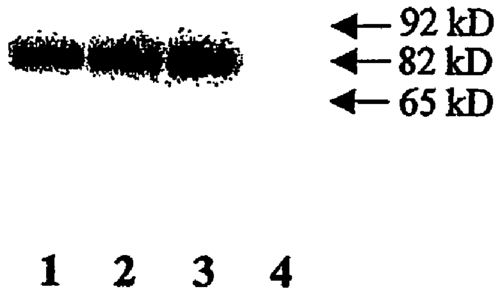
FIG. 1 shows Western blot analysis using protein extract of the cell free supernatant from growth of *Pichia pastoris* KM71H transformed with the pATWAX construct.

In the context of the present application and invention the following definitions apply:

The term "nucleotide sequence" is intended to mean a sequence of two or more nucleotides. The nucleotides may be of genomic, cDNA, RNA, semi synthetic or synthetic origin or a mixture thereof. The term includes single and double stranded forms of DNA or RNA.

The term "deleted and/or substituted" is intended to mean that one or more amino acid residue(s) is/are removed (deleted) from the polypeptide and/or changed (substituted) into another amino acid(s).

The term "nucleotide sequence molecule" is intended to indicate a consecutive stretch of three or more regions of nucleotide sequences. The nucleotide sequence molecule comprises a promoter region, a nucleotide sequence and a non-translated region. The nucleotide sequence or nucleotide sequence molecule may be of genomic, cDNA, RNA, semi-synthetic or synthetic origin, or a combination thereof. The nucleotide sequence molecule is designed to express a nucleotide sequence located within the nucleotide sequence molecule when the nucleotide sequence molecule integrated into the genome or within a microorganism.

The term "promoter region" is intended to mean one or more nucleotide sequences involved in the expression of a nucleotide sequence, e.g. promoter nucleotide sequences, as well as nucleotide sequences involved in regulation and/or enhancement of the expression of the structural gene. A promoter region comprises a promoter nucleotide sequence involved in the expression of a nucleotide sequence, and normally other functions such as enhancer elements and/or signal peptides. The promoter region may be selected from a plant, virus and bacteria or it may be of semi-synthetic or synthetic origin or a mixture thereof as long as it functions in a microorganism. Example of a promoter region is the methanol oxidase promoter, which can be used for the expression of polypeptides in *Pichia pastoris.*

The term "a non-translated region" also called termination region is intended to mean a region of nucleotide sequences, which typically cause the termination of transcription and the polyadenylation of the 3' region of the RNA sequence. The non-translated region may be of native or synthetic origin as long as it functions in a microorganism according to the definition above.

The term "operably linked" is intended to mean the covalent joining of two or more nucleotide sequences by means of enzymatic ligation, in a configuration which enables the normal functions of the sequences ligated to each other. For example a promoter region is operably linked to a signal peptide region and/or a coding nucleotide sequence encoding a polypeptide to direct and/or enable transcription of the coding nucleotide sequence. Another example is a coding nucleotide sequence operably linked to a 3' non-translated region for termination of transcription of the nucleotide sequence. Generally, "operably linked" means that the nucleotide sequences being linked are continuously and in reading frame. Linking is normally accomplished by ligation at convenient restriction sites. If such sites do not exist, synthetic adaptors or the like are used in conjunction with standard recombinant DNA techniques well known for a person skilled in the art.

The term "acyltransferase" is intended to mean a polypeptide, which have the ability to catalyse the transfer of an acyl group from one molecule to another (i.e. interesterification). This transfer involves the breakage of an ester or a thioester bound of the donor molecule and the formation of an ester or thioester bound between the transferred acyl group and the acceptor molecule. Hence, in principal any molecule with an ester/thioester-linked acylgroup can act as a donor molecule and a molecule with at least one hydroxy or a thiol group could act as an acceptor molecule. Commonly occurring donor molecules are acyl-CoA or lipids such as phospholipids and the acyltransferases are in nature known to catalyse e.g., with diacylglycerols, sterols and alcohols as acceptor molecules, the final step in the synthesis of the storage compounds triacylglycerols (TAG), steryl esters and wax esters, respectively.

The term "lipid dependent acyltransferase" is intended to mean an acyltransferase as described above restricted to utilising lipids such as phospholipids, glycolipids, triacylglycerols or other acyl-lipids that could serve as the acyl donor in the acyltransfer reaction. The lecithin: cholesterol acyltransferase (LCAT) (Jonas A., 2000, Biochem. Biophys. Acta 1529: 245-256) and the bacterial glycerophospholipid: cholesterol acyltransferase (GCAT) (Brumlik and Buckley, 1996, J. Bacteriol. 178: 2060-2064) are the only known lipid dependent acyl transferase that has been shown to be functionally active as soluble proteins. All other known lipid dependent acyltransferases are polypeptides with one or several membrane spanning regions and is exemplified by the phospholipid: diacylglycerol acyltransferase (PDAT) and its homologues. It should also be noted that the LCAT enzyme is dependent on an apolipoprotein for functionality. The bacterial GCAT does not show any strong sequence homologies to neither the LCAT nor the PDAT enzymes or to any other known acyltransferases.

The term "membrane independent acyltransferase" are intended to mean an acyltransferase, which is functionally active without being via a membrane-spanning region integrated into a membrane. The "membrane independent acyltransferase" is also active in a water-based environment.

The term "enzymatic conditions" are intended to mean that any necessary conditions available in an environment, which will permit the enzyme to function.

The term "membrane spanning region" is intended to mean part of a polypeptide which anchor the polypeptide into a membrane and is hydrophobic, i.e., the membrane spanning region, such as amino acid residue number 80-96 of the polypeptide shown in SEQ ID NO:1 in the patent application WO 00/60095, as predicted by a hydrophobic plot (Kyte, & Dolittle).

The term "stringent conditions" is intended to mean hybridisation and washing conditions which permits the hybridisation between related nucleotide sequences to be permitted during the hybridisation and remain hybridised during the washing, such as an overnight hybridisation at 42° C. in a solution comprising 50% formamide, 5×SSC (150 mM NaCl, 15 mM trisodium citrate), 50 mM sodium phosphate (pH7.6), 5× Denhardt's solution, 10% dextran sulphate and 20 mg/ml denatured sheared salmon sperm DNA followed by washing the hybridisation membrane or support in 0.1×SSC at approximately 65° C.

The term "acyl donors" are intended to mean phospholipids, triacylglycerols or other molecules containing at least one esterified acyl group that can be donated to an acyl acceptor in the production of fatty acid esters and/or fatty acid thioesters.

The term "acyl acceptors" are intended to mean molecules with at least one hydroxy or thiol group, to which acyl groups derived from the acyl donors can be esterified in the formation of an fatty acid esters or thioesters.

The term "fatty acid esters" are intended to mean fatty acid esters produced by a membrane independent acyltransferase catalysing the formation of ester bounds as described herein from the above mentioned acyl donor and acyl acceptors. Examples of fatty acid esters are acyl-lipids such as triacylglycerols, diacylglycerols, monoacylglycerols, phospholipids, glycolipids, lysolipids etc; waxesters (i.e. fatty acids esterified with long chain alcohols); acylated carbohydrates; acylated amino acids; or any other molecules with at least one acyl group esterified to a hydroxyl group.

The term "stabiliser" is intended to mean any kind of stabilising agent used by persons skilled in the art in order to increase the stability and shelf life time of enzymes.

Nucleotide Sequences Nucleotide Sequence Molecules or Vectors of the Invention

The invention relates to one or more nucleotide sequence(s), derived from a nucleotide sequence encoding an acyltransferase polypeptide comprising at least one membrane-spanning region, encoding an improved active membrane independent acyltransferase polypeptide in which at least one amino acid residue of the membrane-spanning region has been deleted and/or substituted as compared to the original acyltransferase polypeptide, wherein the encoded active membrane independent acyltransferase polypeptide can produce lysolipids and fatty acid esters and/or fatty acid thioesters such as lysophosphospholipid, lysolecithin, triacylglycerols, diacylglycerols, monoacylglycerols, phospholipids, glycolipids, waxesters, acylated carbohydrates and acylated amino acids. By deletion and/or substitution of one or more amino acid residues the encoded polypeptide looses the ability to become integrated into a membrane and remains membrane independent as compared to the original polypeptide. The numbers and/or the location of the amino acid residue(s) to be deleted and/or substituted is/are not critical as long as the polypeptide by the deletion and/or substitution become membrane independent. Part of the membrane-spanning region may be present as long as it does not integrate or attach the polypeptide to a membrane. The polypeptide encoding the membrane independent acyltransferase named ATWAX is a membrane independent acyltransferase which may be encoded by a nucleotide sequence, originally encoding an integral membrane protein with one or several membrane spanning regions wherein one or several of the membrane spanning regions has/have been deleted and/or substituted. The nucleotide sequence may also be synthetic or semi synthetic as long as it has the function of a membrane independent acyltransferase which may be used in the formation of fatty acid esters, like acyl-lipids such as triacylglycerols, diacylglycerols, monoacylglycerols, phospholipids, glycolipids, lysolipids etc; waxesters (i.e. fatty acids esterified with long chain alcohols); acylated carbohydrates; acylated amino acids; or any other molecules with at least one acyl group esterified to a hydroxyl group. The nucleotide sequence encoding the acyltransferase may be derived from a nucleotide sequence encoding a lipid dependent acyltransferase polypeptide, such as a nucleotide sequence encoding an lipid dependent acyltransferase polypeptide catalysing an acyl transfer reaction in which acylphospholipids acts as acyl donors, for example a nucleotide sequence encoding a phospholipid: diacylglycerol acyltransferase.

Such nucleotide sequences may be obtained from different kind of species such as bacteria, yeasts, fungi, plants, insects or mammalians. Examples are *Arabidopsis thaliana, Crepis palaestina, Euphorbia lagascae, Saccharomyces cerevisiae, Schizosaccharomyces pombe, Aspergillus strains*, e.g. *A. niger, A. nidulans, A. fumigatus, A. sojae, Pichia strains*, such as *P. Pastoris* or *P. methanolica Mucor* strains, e.g. *M. circinelloides, Hansenula*, such as *H. Polymorpha* and *Trichoderma, Klyveromyces*, or *Yarrowia*. Examples on nucleotide sequences are shown in SEQ ID NO:1, 4, 8, 10, 12, 14, 15, 16, 18 or 20.

According to one embodiment the invention relates to a nucleotide sequence, wherein from 1 to 291 nucleotide sequence residue(s) has/have been deleted and/or substituted from the nucleotide sequence shown in SEQ ID NO:1. The number(s) of nucleotide sequence residues to be deleted is/are chosen in such a way that the open reading frame of the nucleotide sequence encoding the membrane independent acyltransferase polypeptide is not disturbed and the membrane spanning region corresponding to nucleotide sequence 238 to 288 is deleted and/or substituted. One example is the nucleotide sequence shown in SEQ ID NO:2, where 290 nucleotide sequence residues have been deleted and/or substituted resulting in the membrane independent acyltransferase polypeptide shown in SEQ ID NO:3.

According to another embodiment the invention relates to a nucleotide sequence, wherein from 1 to 219 nucleotide sequence residue(s) of the 5'-end has/have been deleted and/or substituted from the nucleotide sequence shown in SEQ ID NO: 4, 1-87 nucleotide sequence residue(s) of SEQ ID NO:8 and SEQ ID NO:10 and 1-190 nucleotide sequence residue(s) of SEQ ID NO:12.

According to another embodiment the invention relates to a nucleotide sequence, wherein at least the nucleotide sequence residues 142 to 210 have been deleted and/or substituted from the nucleotide sequence shown in SEQ ID NO:4, 19-87 nucleotide sequence residues of SEQ ID NO 8 and SEQ ID NO:10 and 130-190 nucleotide sequence residues of SEQ ID NO:12.

According to another embodiment the invention relates to a nucleotide sequence, wherein from 1 to 228 nucleotide sequence residue(s) of the 5'-end has/have been deleted and/or substituted from the nucleotide sequence shown in SEQ ID NO: 16, 1-219 nucleotide sequence residue(s) of SEQ ID NO:18 and 1-261 nucleotide sequence residue(s) of SEQ ID NO:20.

According to another embodiment the invention relates to a nucleotide sequence, wherein at least the nucleotide sequence residues 169 to 228 have been deleted and/or substituted from the nucleotide sequence shown in SEQ ID NO:16, 151-219 nucleotide sequence residue(s) of SEQ ID NO:18 and 193-261 nucleotide sequence residue(s) of SEQ ID NO:20.

The number(s) of nucleotide sequence residues to be deleted is/are chosen in such a way that the open reading frame of the nucleotide sequence encoding the membrane independent acyltransferase polypeptide is not disturbed and the membrane spanning region are removed/deleted.

According to one embodiment of the invention the nucleotide sequence encoding the membrane independent acyltransferase polypeptide may hybridise under stringent conditions to a nucleotide sequence as shown in SEQ ID NO:1, 2, 4, 6, 8, 10, 12, 14, 15, 16, 18 or 20. Furthermore the nucleotide sequence as shown in SEQ ID NO: 1, 2, 4, 6, 8, 10, 12, 14, 15, 16, 18 or 20 may be different as compared to another nucleotide sequence due to the degeneracy of the genetic code.

Additionally the nucleotide sequence encoding the membrane independent acyltransferase polypeptide may at least show 75%, 80%, 85%, 90% or 95% homology to the amino acid sequence(s) shown in SEQ ID NO:3, 7, 9, 11, 13, 17, 19, 21 or a homologue thereof.

Furthermore, the nucleotide sequence shown in SEQ ID NO 2, encoding the membrane independent acyltransferase polypeptide shown in SEQ ID NO 3, may be modified by removing (deleting) nucleotides, encoding one or several amino acid residues in the N-terminal part corresponding to the first 71 amino acid residues of the polypeptide shown in SEQ ID NO 3, with maintained acyltransferase activity. Furthermore one or more amino acid residues may be substituted as long as the acyltransferase activity remains. Methods, which are suitable for the removal (deletion) of a specific nucleic acid sequence are well known for a person skilled in the art and includes methods such as PCR.

Moreover, the amino acid residues S229, D472, and H523 shown in SEQ ID NO 3 are essential for activity as described in the examples and is here suggested to be part of the a catalytic triad in the active site of the enzyme.

Additionally, the invention relates to an oligonucleotide, which specifically hybridise under stringent conditions to the nucleotide sequence(s) and/or the nucleic acid molecule(s) described herein. The oligonucleotide may be used for the detection of the nucleotide sequence and/or the nucleotide sequence, such as the presence of the nucleotide sequence within a host cell.

According to another embodiment the invention relates to a nucleotide sequence molecule, which comprises at least one promoter region which functions in a host. The promoter region is operably linked to at least one nucleotide sequence as described above, which is operably linked to at least one non-translated region which functions in a host. Furthermore, a signal peptide may be present between the promoter region and the nucleotide sequence as described above.

The nucleotide sequence molecule may be present in a vector, such as an expression vector, which may be used for the production of the polypeptide, which has acyltransferase activity. The vector is typically derived from plasmid or viral DNA. A number of suitable expression vectors for expression in the host cells mentioned herein are commercially available or described in the literature. Any kind of vector may be used as long as it functions in a host cell which is capable of performing glycosylation of the polypeptide, such as vectors which functions in yeast. Useful expression vectors for yeast cells include the 2μ plasmid and derivatives thereof, the POTI vector (U.S. Pat. No. 4,931,373), the pJSO37 vector described in Okkels, Ann. New York Acad. Sci. 782, 202-207, 1996, and pPICZ A, B or C (Invitrogen).

Other vectors for use in this invention include those that allow the nucleotide sequence encoding the polypeptide to be amplified in copy number. Such amplifiable vectors are well known in the art. They include, for example, vectors able to be amplified by DHFR amplification (see, e.g., Kaufman, U.S. Pat. No. 4,470,461, Kaufman and Sharp, "Construction Of A Modular Dihydrafolate Reductase cDNA Gene: Analysis Of Signals Utilized For Efficient Expression", Mol. Cell. Biol., 2, pp. 1304-19 (1982)) and glutamine synthetase ("GS") amplification (see, e.g., U.S. Pat. No. 5,122,464 and EP 338, 841).

The vector may further comprise a DNA sequence enabling the vector to replicate in the host cell in question. When the host cell is a yeast cell, suitable sequences enabling the vector to replicate are the yeast plasmid 2μ replication genes REP 1-3 and start of replication.

The vector may also comprise a selectable marker, e.g., a gene the product of which complements a toxin related deficiency in the host cell, such as the gene coding for dihydrofolate reductase (DHFR) or the *Schizosaccharomyces pombe* TPI gene (described by P. R. Russell, Gene 40, 1985, pp. 125-130), or one which confers resistance to a drug, e.g., ampicillin, kanamycin, tetracyclin, chloramphenicol, neomycin, hygromycin, zeocin or methotrexate. For *Saccharomyces cerevisiae*, selectable markers include ura3 and leu2. For filamentous fungi, selectable markers include amdS, pyrG, arcB, niaD and sC.

The term "control sequences" is defined herein to include all components, which are necessary or advantageous for the expression of the polypeptide of the invention. Each control sequence may be native or foreign to the nucleic acid sequence encoding the polypeptide. Such control sequences include, but are not limited to, a leader sequence, signal peptide, polyadenylation sequence, propeptide sequence, promoter (inducible or constitutive), enhancer or upstream activating sequence, signal peptide sequence, and transcription terminator. At a minimum, the control sequences include a promoter. Examples of suitable control sequences for use in yeast host cells include the promoters of the yeast α-mating system, the yeast triose phosphate isomerase (TPI) promoter, promoters from yeast glycolytic genes or alcohol dehydrogenase genes, the ADH2-4c promoter, and the inducible GAL promoter. Examples of suitable control sequences for use in filamentous fungal host cells include the ADH3 promoter and terminator, a promoter derived from the genes encoding *Aspergillus oryzae* TAKA amylase triose phosphate isomerase or alkaline protease, an *A. niger* α-amylase, *A. niger* or *A. nidulans* glucoamylase, *A. nidulans* acetamidase, *Rhizomucor miehei* aspartic proteinase or lipase, the TPI1 terminator and the ADH3 terminator.

The presence or absence of a signal peptide will, e.g., depend on the expression host cell used for the production of the polypeptide to be expressed (whether it is an intracellular or extra cellular polypeptide) and whether it is desirable to obtain secretion. For use in filamentous fungi, the signal peptide may conveniently be derived from a gene encoding an *Aspergillus* sp. amylase or glucoamylase, a gene encoding a *Rhizomucor miehei* lipase or protease or a *Humicola lanuginosa* lipase. The signal peptide is preferably derived from a gene encoding *A. oryzae* TAKA amylase, *A. niger* neutral α-amylase, *A. niger* acid-stable amylase, or *A. niger* glucoamylase. For use in yeast cells suitable signal peptides have been found to be the α-factor signal peptide from *S. cereviciae* (cf. U.S. Pat. No. 4,870,008), a modified carboxypeptidase signal peptide (cf. L. A. Valls et al., Cell 48, 1987, pp. 887-897), the yeast BAR1 signal peptide (cf. WO 87/02670), the yeast aspartic protease 3 (YAP3) signal peptide (cf. M. Egel-Mitani et al., Yeast 6, 1990, pp. 127-137), and the synthetic leader sequence TA57 (WO98/32867).

Furthermore the invention relates to an oligonucleotide, which hybridises under stringent conditions (as defined above) to a nucleotide sequence and/or a nucleotide sequence molecule as described above.

Host Cells Method and Polypeptide of the Invention

Any suitable host cell may be used for the maintenance and production of the vector of the invention as long as the host is capable of producing a glycosylated product. The host cell may be a eukaryotic cell, for example fungi, yeast, insects and mammalian cells. A eukaryotic system may provide significant advantages compared to the use of a prokaryotic system, for the production of certain polypeptides encoded by nucleotide sequence molecules and/or vectors present within the host cell or integrated into the genome of the host cell. For example, yeast can generally be grown to higher cell densities than bacteria and may be capable of glycosylating expressed polypeptides, where such glycosylation is important for a proper folding of the polypeptide and/or catalytic activity of the polypeptide.

The host cell may be a host cell belonging to a GMP (Good Manufacturing Practice) certified cell-line. Examples of suitable filamentous fungal host cells include strains of *Fusarium, Trichoderma, Aspergillus*, e.g. *A. oryzae, A. niger*, A. sojae or *A. nidulans, Mucor*, e.g. M circinelloides. Examples of suitable yeast host cells include strains of *Saccharomyces*, e.g. *S. cerevisiae, Schizosaccharomyces*, Klyveromyces, *Pichia*, such as *P. Pastoris* or *P. methanolica, Hansenula*, such as *H. Polymorpha* or *Yarrowia*. Examples of *P. Pastoris* strains are X-33, KM71H, and GS115 which may be obtained from Invitrogen Inc. *Pichia pastoris* is a methylotrophic yeast which can grow on methanol as a sole carbon and energy source (Ellis et al., 1985). *P. pastoris* is also amenable to efficient high cell density fermentation technology. Therefore is *Pichia pastoris* a suitable host for expression of heterologous protein in large quantity, with a methanol oxidase promoter based expression system (Cregg et al., 1987). Additional suitable donor cell lines are known in the art and available from public depositories such as the American Type Culture Collection, Rockville, Md.

The vector is transferred (introduced) into the host cell using a suitable method dependent on which host cell has been selected. The introduction of the vector harbouring the nucleotide sequence molecule into fungal cells may be by a method involving protoplast formation, transformation of the protoplasts, and regeneration of the cell wall in a manner known per se. Suitable procedures for transformation of *Aspergillus* host cells are described in EP 238 023 and U.S. Pat. No. 5,679,543. Suitable methods for transforming *Fusarium* species are described by Malardier et al., 1989, *Gene* 78: 147-156 and WO 96/00787. Yeast may be transformed using the procedures described by Becker and Guarente, In Abelson, J. N. and Simon, M. I., editors, *Guide to Yeast Genetics and Molecular Biology, Methods in Enzymology*, Volume 194, pp 182-187, Academic Press, Inc., New York; Ito et al., 1983, *Journal of Bacteriology* 153: 163; Hinnen et al., 1978, *Proceedings of the National Academy of Sciences USA* 75: 1920: and as disclosed by Clontech Laboratories, Inc, Palo Alto, Calif., USA (in the product protocol for the Yeastmaker™ Yeast Transformation System Kit) or by using the *Pichia* Manual supplied by Invitrogen Inc. These methods are well known in the art and e.g., described by Ausbel et al. (eds.), 1996, Current Protocols in Molecular Biology, John Wiley & Sons, New York, USA.

In the production methods (process) of the present invention, the cells are cultivated in a growth medium suitable for maintenance and/or production of the nucleotide sequence molecule and/or the vector using methods known in the art. For example, the cell may be cultivated by shake flask cultivation, small-scale or large-scale fermentation (including continuous, batch, fed-batch, or solid state fermentations) in laboratory or industrial fermenters performed in a suitable growth medium and under conditions allowing the vector, nucleotide sequence molecule or polypeptide to be expressed and/or isolated. The vector, nucleotide sequence molecule or the polypeptide may be used in the chemical or in the pharmaceutical industry. The cultivation takes place in a suitable growth medium comprising carbon and nitrogen sources and inorganic salts, using procedures known in the art. Suitable growth media are available from commercial suppliers or may be prepared according to published compositions (e.g., in catalogues of the American Type Culture Collection). The cultivation of *Pichia pastoris* is performed using the method described in EXAMPLE 2 or any other suitable method. After cultivation, the polypeptide is recovered from the culture medium, the cells or after separating the cells from the culture medium. The recovered polypeptide encodes an active membrane independent acyltransferase without the ability to become integrated into a membrane, i.e., one ore more of the amino acid residue(s) present in the membrane spanning region has/have been deleted and/or substituted. Examples of methods are those mentioned in Maniatis et al., Molecular Cloning: A Laboratory Manual (Cold Spring Harbour Press) (1989) and Qiagen Inc.

According to another embodiment the polypeptide is an acyltransferase active at a pH ranging from about 4 to about 10, and stable at a temperature below about 60° C. The enzymatic activity of the polypeptide can be measured using the assay method described in EXAMPLE 4 or EXAMPLE 5.

The polypeptide may furthermore be immobilised to a carrier. Suitable carriers and methods for the immobilisation of the polypeptide to the carrier are well known for a person skilled in the art (Tisher, W., & Kasche, V., 1999, Trends Biotechnol. 17(8): 326-335).

According to one embodiment of the invention the polypeptide named ATWAX and described above may be lyophilised and/or freeze-dried. Lyophilisation and/or freeze-drying may be performed using conventional techniques known for a person skilled in the art.

A further embodiment relates to the use of a nucleotide sequence and/or a nucleotide sequence molecule and/or a vector and/or a host cell and/or the methods and/or the polypeptide of the invention. The polypeptide may be used for the production of fatty acid esters. Examples of fatty acid esters are acyllipids such as triacylglycerols, diacylglycerols, monoacylglycerols, phospholipids, glycolipids, lysolipids; waxesters; acylated carbohydrates; acylated amino acids; or any other molecules with at least one acyl group esterified to a hydroxyl group are fatty acid esters.

Examples of products which may be produced by the method are fatty acid esters used in cosmetics, foods, food additives, dairy products, confectionary, flavours, bakery, pharmaceuticals, candles, soaps, detergents, laundries, polymers, coatings, plasticizer-, drying oils, lubricants, varnishes, linoleum, printing, inks, textile dyes and surfactants.

Examples of what the invented polypeptide may be used for are listed below.

Production of Structured Lipids

The invented polypeptide(s) are suitable to be used in the production of structured lipids without the need of organic solvents, which would be both environmentally favourable, healthier and eliminates one or more purification steps after the production of the structured lipids. Additionally, it may be easier to get an approval by the authorities for such a product, manufactured in a process without the use of organic solvents. The positional distribution of acyl groups differing in length and degree of saturation in the triacylglycerol molecule is known to be important regarding nutritional and health aspects partly due to differences in digestibility and absorbability. As an example most triacylglycerols of vegetable origin are highly unsaturated at the 2-position, mainly oleic and linoleic acid. However, in human milk fat the saturated fatty acid palmitic acid is highly enriched at the 2-position and it is known that such type of fat is more easily absorbed and utilized by infants. Structured triacylglycerols mimicking the properties of triacylglycerols in the human milk fat can be manufactured in a process in which ATWAX catalyses the transfer of acyl groups from the sn2 position of lecithin to monoacylglycerol with palmitic acid at the sn2 position (2-palmitoyl glycerol), yielding triacylglycerols enriched with unsaturated fatty acids such as oleic and linoleic acid in the 1-, 3-positions and palmitic acid in the 2-position. The source of the 2-palmitoyl glycerol for use in this process may be obtained by 1, 3 specific lipase hydrolyses of palm oil enriched in triacylglycerols with palmitic acid at the 2-position.

In another application structured lipids are used as fat replacers in low calorie foods. Acylglycerols with an acetyl group at the 2-position are used as fat replacers in low calorie foods such as dairy products, bakery, cereals, pasta, cheese, tofu, chocolate, chocolate confections, margarine, salted snacks, sour cream, spreads etc. This diet fat can be manufactured in a process in which ATWAX catalyse the transfer of acyl groups from the sn2 position of lecithin to 2-acetyl glycerol. In a similar manner, structured diacylglycerols can be produced by an acyltransfer of fatty acids from an acyldonor such as lecithin to glycerol as the acceptor molecule. The major product in such a process is 1,3-diacylglycerol (i.e. diacylglycerol with acyl groups at the sn1 and sn2 position), since the ATWAX enzyme has preferences for the acylation of the sn 1 and sn3 positions of the glycerol molecule. ps Production of Fat-Soluble Molecules.

The invented polypeptide(s) are suitable to be used to render molecules more hydrophobic by coupling fatty acids via an acylation reaction to molecules that otherwise are badly soluble in hydrophobic solvents such as fats and oils. Example of such modification, is the acylation of water soluble flavours and vitamins which makes these fatty acid esters of flavours and vitamins more fat soluble and hence more suitable for certain applications such as food, cosmetic, and pharma applications. As an example fatty acid esters of vitamins such as vitamin E (tocopherol) are used in skin-care products since the vitamins are more readily adsorbed into the skin. In certain food applications it is desirable to make water-soluble flavours, vitamins or other additives are more easily mixed into fatty foodstuffs. In a process involving ATWAX the manufacturing of fatty acid esters by the acylation of hydrophilic molecules possessing a hydroxyl group can be performed by an acyltransfer catalysed by ATWAX. The acyl donor molecule in this reaction can be lecithin or phospholipids or any other suitable acyl-lipids.

Removal of Undesirable Fat.

The invented polypeptide(s) are suitable to be used enables the removal of one or more fatty acids from a molecule by the use of ATWAX, such as by transferring one or more fatty acids from a molecule to an acceptor molecule such as monoacylglycerol, diacylglycerol. Phospholipids present within milk and dairy products are examples of molecules from which one fatty acid may be removed are. The major phospholipids present in milks from mammals are phosphatidylcholine, phosphatidylethanolamine and sphingolipids, each comprising about 30% of the total phospholipids present. These phospholipids are part of the milk fat globule membrane fraction, which constitutes a minor part of the whole milk lipids. Apart from the phospholipids this membrane lipid fraction also contains TAG, diacylglycerol and monoacylglycerol.

It is desirable to remove fatty acids, especially unsaturated fatty acids such as oleic, linoleic, and linolenic acid from milk prior to use of the milk in products such as low fat or non fat products. During storage the unsaturated fatty acids that are mainly present on the sn2-position of the phospholipids, becomes oxidised and thus the milk product becomes rancid with a bad smell and taste (off-flavour). Today, there is no suitable method for removal of these undesirable fatty acids from milk. By the addition of ATWAX to milk the fatty acid on the sn2 position of the phospholipid is transacylated to the acceptor molecule such as monoacylglycerol and/or diacylglycerol by which triacylglycerol is produced. This formed TAG will be removed together with the main TAG, in the production of low fat or non-fat product such as dry milk powder, cheese, yoghurt and other dairy products. Thereby the off-flavouring is reduced and/or eliminated and the shelf life time of the products could be increased.

Furthermore, in the transfer of fatty acids in milk from the phospholipids to acceptor molecules such as monoacylglycerols or diacylglycerols, the phospholipids will be converted to lysophospholipids. With an increased fraction of lysophospholipids, the membrane lipid fraction is more easily disintegrated and the encapsulated TAG is released. This released fraction of TAG as well as the TAG that is formed in the transfer of fatty acids from lecithin to monoacylglycerols and/or diacylglycerol will be removed together with the main TAG fraction. Thereby a process, in production of low-fat or non-fat milk products, involving the use of ATWAX can more efficiently reduce the fat content in such milk products.

Another field of application is to use ATWAX to remove phospholipids e.g. lecithin. In the refining of vegetable oils, the removal of the lecithin fraction, i.e. degumming is an important process in the production of high quality oils. In a refining process involving the use of ATWAX, lecithin present in the oil can be converted into lysolecithin, which will be removed from the oil into the water phase. The fatty acid removed from the lecithin in this process will be transferred to an acceptor molecule present in the oil such as diacylglycerol by which triacylglycerol is formed.

Modification of Lipids Presents in Animal and Plant Raw Material.

In the field of baking, bread improvers such as emulsifiers based on lipids are commonly used. However, these emulsifiers are known to give off-flavour and also caking and lumping problems, especially in hot and humid climates. In flour, such as wheat flour, polar lipids mainly lecithin and galactolipid (e.g. digalctosyldiacylglycerol) are present. In a baking process in which ATWAX is added, the lecithin and the galactolipid deriving from the flour, can enzymatically be converted into the corresponding lysolipids. This conversion of the polar lipids into lysolipids are known to give a similar stabilising effect of the dough as what is achieved with the today commonly added emulsifiers such as diacetyl tartaric acid esters of monoacylglycerols. Therefore the ATWAX enzyme can totally or partly replace the use of emulsifiers in the baking process and thus reduce the problems with off-flavour and the tendency of lump formation.

In a similar manner the conversion of lecithin or phospholipids present in “raw materials” such as milk, flour, eggs, soy protein, cocoa, or any other animal or plant materials into lysolecithin or lysophospholipids can be executed in a process involving ATWAX. In such as process important properties of the raw material are modulated, such as amphiphilic nature, texture, melting point, viscosity, flavour, emulsification, foaming, and wetting, to be suited for the production of a certain complex foodstuffs. Thereby, the need for food additives such as emulsifiers, wetting agents, dough strengtheners, and film formers are reduced.

Kit of the Invention

A kit comprising the polypeptide which has the enzymatic activity of a (membrane independent) acyltransferase and the membrane spanning region removed or a fragment thereof or a kit in which the polypeptide has been immobilised on a carrier. The polypeptide may be provided in the kit as lyophilised or freeze dried. The kit may also comprise components, which are essential for the stability and activity of the polypeptide, such as a stabiliser. The kit may furthermore comprise a manual with instructions for the use of the polypeptide.

The following examples are intended to illustrate but not to limit the invention in any manner, shape, or form, either explicitly or implicitly.

EXAMPLES

Example 1

Amplification of Nucleotide Sequences, Homologues to the *Saccharomvees cerevisiae* Gene LRO1, for Expression in *Pichia pastoris.*

Nucleotide sequences were amplified from a plasmid template (pBluescript, Stratagene Inc.) containing the intact yeast gene LRO1, encoding a phospholipid: diacylglycerol acyltransferase (PDAT) with one membrane-spanning region, (described in Dahlqvist et al., 2000, PNAS 97:6487-6492) by thermo stable Pfu Turbo Polymerase (Stratagene Inc.). A set of primers was designed for the amplification of three different nucleotide sequences A, B, and C, identical in nucleotide sequence to the part of the LRO1 gene encoding the amino acid residues 98 to 661, 170 to 661 and 190 to 661 respectively. The forward (5' end) primers used for this PCR reaction were for the sequences A, B, and C; 5'CCATGGGAATGAATTCATGGCTTATCATGTTCATAATAGCGATAGC3' (SEQ ID NO; 22), 5'CCATGGGAATGAATTCCGAGGCCAAACATCCTGTTGTAATG3' (SEQ ID NO: 23), and 5'CCATGGGAATGAATTCGGAGTTATTGGAGACGATGAGTGCGATAGT3'(SEQ ID NO: 24)respectively.

The oligonucleotide sequence, 5' GCCTCCTTGGGCGGCCGCTCACATTGGGAGGGCATCTGAGAAAC3' (SEQ ID NO: 25) was used as the reverse (3' end) primer in all the three PCR amplifications. The three amplified nucleotide sequences all lack the sequence region, present in the LRO1, which encodes a transmembrane region. The amplified nucleotide sequence A is shown in SEQ ID NO 2.

Additionally one nucleotide sequence was amplified resulting in the nucleotide sequence D with nucleotides encoding 6-residue histidine at the N-terminus in frame with the region encoding the amino acid residues 98 to 661 of the yeast PDAT. This was achieved by first sub cloning the amplified nucleotide sequence A above into the NheI and XhoI sites of the plasmid pET28a(+) and then using the following oligonucleotide primers for PCR amplification; 5'CCATGGGAATGAATTCATGGGCAGC AGCAGCCATCATCAT3' (SEQ ID NO: 26) and 5'GCCTCCTTGGGCGGCCGCTCACATTGGGAGG GCATCTGAGAAAC3'(SEQ ID NO: 27).

The amplified PCR products A, B, C, and D above, were purified, digested by EcoRI and NotI, and subcloned between the EcoRI and NotI sites of the *Pichia* expression vector PpicZ□A in frame with the sequence encoding the □□factor signalpeptide present in the expression vector. The resultant *Pichia* expression vectors are named pATWAX, p72ATWAX, p92ATWAX, and pHISATWAX, with inserts encoding the polypeptides ATWAX, 72ATWAX, 92ATWAX, and HISATWAX respectively. These vectors were linearized using unique SacI restriction site for transformation in *Pichia pastoris* host strain.

Site directed mutagenesis of the ATWAX polypeptide sequence described in SEQ ID NO: 2 were performed in order to identify the catalytic triad. The PCR based mutagenesis were performed using mega-primer method (Ling, M. M., & Robinson, B. H., 1997, 254(2): 157-178) for the construction of three nucleotide sequences encoding ATWAX-S229A, ATWAX-D472N and ATWAX-H523A with the single residue mutant S229A, D472N and H523A, respectively.

Example 2

Transformation in *Pichia* and Growth for Expression.

Competent *Pichia pastoris* cells were prepared according to the procedure mentioned in the EasySelect Manual supplied by Invitrogen Inc. Electroporation, as described in the EasySelect Manual, was used to transform the linearized expression vector, pATWAX, p72ATWAX, p92ATWAX or pHISATWAX described in EXAMPLE 1 above, into the Pichiapastoris host strain X-33 or KM71H. The procedure of Zeocin selection was used to select transformants, which were plated on YPD medium containing Zeocin. For the expression of the transformed genes, cells were initially cultured to a final O.D. of 3-5 in BMGY medium supplemented with 1% (v/v) glycerol, after which cells were subsequently washed with either sterile water or YPD medium. The washed cells were then suspended in BMMY medium supplemented with 0.5% (v/v) methanol for induction of the transgene and further cultured for 3-4 days in a volume corresponding to 0.5-0.2 of the original volume. Methanol (20%, v/v) was added to a final concentration of 0.5% (v/v) every 24 hours. Cell-free medium was collected by centrifugation and was used for western blot analyses and enzyme activity studies.

Example 3

Western Blot Analysis of Cell Free Medium of *Pichia pastoris* KM71H Transformed with pATWAX.

In order to determine the presence of ATWAX in the cell free culture medium, *P. pastoris* KM71H transformed with pATWAX were cultured as described in EXAMPLE 2. Aliquots of cell free culture medium were withdrawn at different time points following induction and subjected to Western blot analysis using anti yeast-PDAT polyclonal antibody. The antibody was raised in a rabbit by the injection of partially purified ATWAX. The ATWAX used for this purpose was produced in *Echerichia coli.*

The western blot based on immunodetection system as presented in FIG. 1 clearly show the presence of a polypeptide, present in the cell free medium with a molecular weight of approximately 82 kDa, that cross-reacts with the anti-yeast PDAT. By comparing the results obtained on the western blot analyses obtained with the cell free medium from 58, 82 and 112 hours of induction (i.e. FIG. 1 lane 1, 2, and 3, respectively) it is concluded that the secreted ATWAX is continuously secreted and accumulated in the cell free medium up to at least 112 hours of induction without being degraded. This is further supported by the lack of additional band of lower molecular weight that could be referred to as degradation products. Cell free medium of the untransformed *Pichia* strain did not crossreact with the ATWAX antibody (laneS). These data also indicates that the ATWAX present in the cell free medium is glycosylated and that the glycosylation contributes to about 17 kDa of the molecular weight, since a non-glycosylated ATWAX should have a weight of 65 kDa as calculated from its amino acid composition.

Example 4

Detection of ATWAX Enzyme Activity in the Culture Supernatants.

Figure 2:
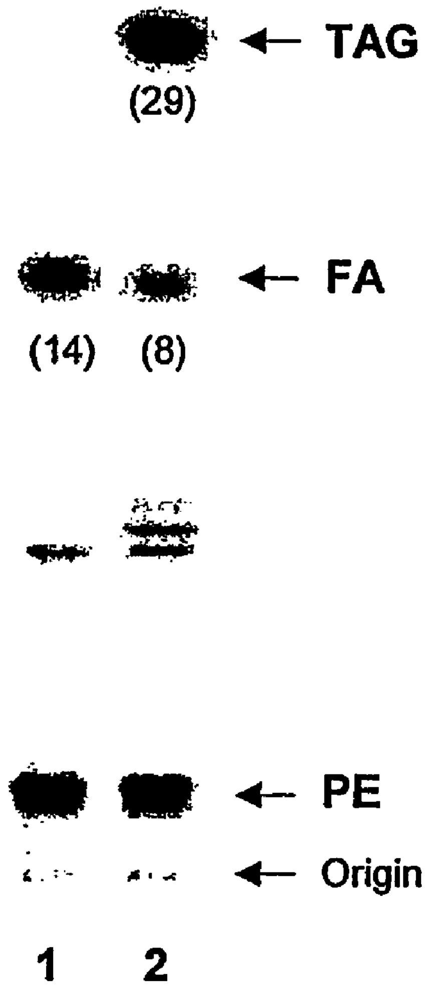
FIG. 2 shows the synthesis of triacylglycerol catalysed by the membrane independent acyltransferase (ATWAX), as visualized by autoradiography of lipid products separated on TLC.

To determine the enzyme activity in the cell free culture medium the cell free supernatant was assayed for enzyme activity as follows. The cell free supernatant of the induced cultures described in EXAMPLE 2, from 116 hours of growth of *Pichia pastoris* KM71H transformed with the pATWAX construct encoding ATWAX, the polypeptide described in SEQ ID NO: 2 (FIG. 2, lane 2) and the congenic wt strain (FIG. 2, lane 1) were assayed for acyl transferase activity. Lipid substrate, sn1-palmitoyl sn2-[$^{14}$C]linoleoyl-phosphatidylethanolamine (5 nmol; 5000 dpm/nmol) and dioleoylglycerol (2.5 nmol) dissolved in chloroform was aliquoted in 1.5 ml tubes and the chloroform was evaporated under a stream of $N_2$ (g). After addition of 20 ul 0.25 M potassium phosphate, pH 7.2, the mixture was violently agitated and 80 ul of cell free supernatant was added and incubated at 30° C. for 90 min. Lipids were extracted from the reaction mixture into chloroform (Bligh, E. G. and Dyer, W. J (1959) Can. J. Biochem. Physiol. 37, 911-917) and separated by TLC on silica gel 60 plates (200×200 mm) in chloroform/methanol/acetic acid/water (85:15:10:3.5) migrating 90 mm using an automatic developing chamber (Camag). The plate was dried and redeveloped in hexane/diethyl ether/acetic acid (80:20:1) with a solvent migration of 180 mm. The radioactive lipids were visualized and quantified on the plates by electronic autoradiography (Instant Imager; Packard). As a control, the enzyme activity in the cell free supernatant of the wild type host strain culture was analysed. As shown in FIG. 2, the majority of the [$^{14}$C]linoleoyl group translocated from phosphatidylethanolamine is associated with triacylglycerol after the incubation. This demonstrates that the truncated membrane independent form of yeast PDAT, referred to as a membrane independent acyltransferase that we have named ATWAX, is able of catalysing the formation of TAG by an acyltransfer from phosphatidylethanolamine to diacylglycerol (DAG). Radiolabeled acylgroups can also be detected as unesterified fatty acids indicating the presence of a lipase activity. However, since a release of radiolabeled fatty acids also occur in the cell free supernatant of untransformed host strain it is not possible to conclude whether this lipase activity is associated with ATWAX.

The cell free supernatant of the induced cultures of *P. pastoris* KM71H transformed with the p72ATWAX or p92ATWAX constructs were by western blot analyses shown to be expressed and secreted in to the culture medium. However the cell free medium containing these truncated polypeptides, lacking a stretch of 72 or 92 amino acids residues of the ATWAX N-terminus, respectively, did not catalyse the synthesis of TAG when analysed for enzyme activity according to method described above.

Furthermore, nucleotide sequences encoding the ATWAX-S229A, ATWAX-D472N and ATWAX-H523A mutant polypeptides were generated as described in EXAMPLE 1 and expressed in *Pichia pastoris* as described in EXAMPLE 2. The expression of these mutant polypeptides was verified by western blot analyses of aliquots of cell free medium from cultures expressing these polypeptides, respectively. However, all three mutant polypeptides were inactive when assayed for acyltransferase activity according to method described above. Hence, the amino acid residues S229, D472 and H523 are essential for the catalytic activity and are therefore here suggested to be part of a catalytic triad.

A membrane independent acyltransferase with an N-terminal stretch of six Histidine residues was produced by the expression of the construct HisATWAX in *Pichia pastoris* (described in EXAMPLE 1 and 2). This polypeptide was when analysed for acyltransferase activity as described above shown to be active with similar catalytic properties as the ATWAX.

Example 5

Production of Waxesters

Wax esters can be synthesised from soy lecithin and different alcohols by the catalyses of the membrane independent acyltransferases, ATWAX and HisATWAX. This acyltransferases was produced and secreted into the culture medium by expressing the construct pATWAX or pHisATWAX, respectively in *Pichia pastoris* (described in EXAMPLE 2). Aliquots of cell free medium was prepared and stored at −20° C.

Figure 3:
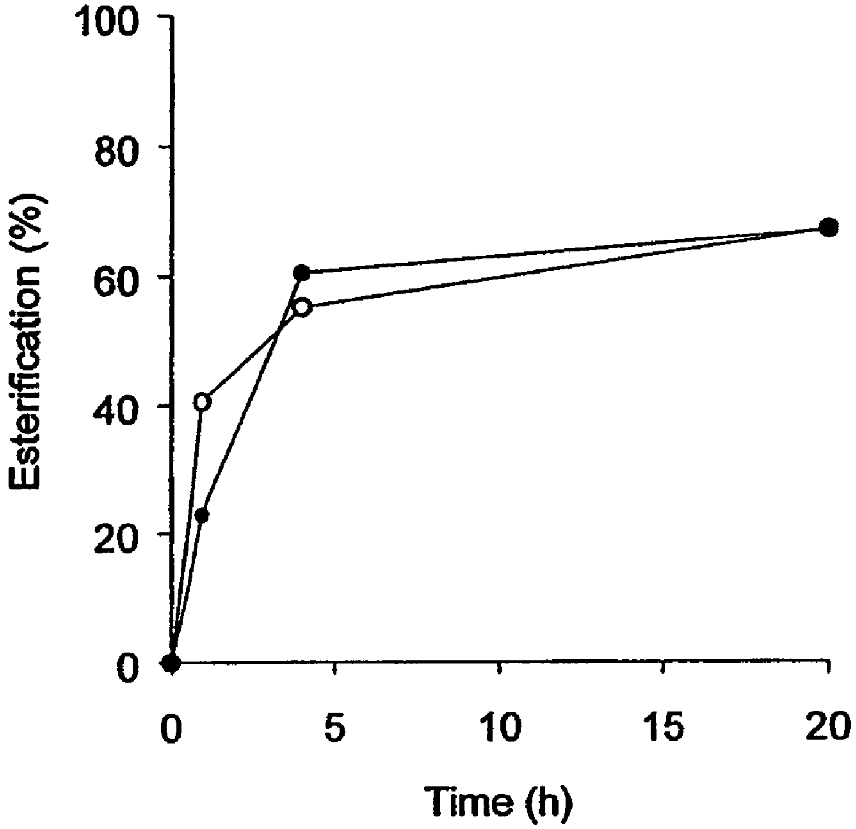
FIG. 3. shows the time course of the wax esters synthesises from added soy lecithin and 13c-docosenoyl-alcohol (○) or ricinoleoyl-alcohol (●) in cell free medium of *Pichia pastoris* cultures expressing the membrane independent acyltransferase HisATWAX as described in EXAMPLE 5.

The ability to synthesise wax esters from soy lecithin and 13c-docosenoyl-alcohol (○ in FIG. 3) or ricinoleoyl-alcohol (● in FIG. 3) by the membrane independent His-tagged acyltransferase present in the cell free culture medium was investigated and the results are given in FIG. 3. The conditions for the synthesis were as follows; lecithin (2.5 mg), sn1-oleoyl-sn2-[$^{14}$C]oleoyl-phosphatidylcholine (5 nmol; 5000 dpm/nmol) and 6 mmol of 13c-docosenoyl-alcohol or ricinoleoyl-alcohol dissolved in chloroform was aliquoted in 12 ml glass tubes and the chloroform was evaporated under a stream of $N_2$ (g). To the dry lipid substrate 0.5 ml of cell free medium and 25 ul 1.0 M potassium phosphate, pH 7.2 were added. The reaction mixture was sonicated in a water bath (Branson 2510) for 30 min and was further incubated at 37° C. to a final incubation time as indicated in FIG. 3. Lipids were extracted from the reaction mixture into chloroform (Bligh, E. G. and Dyer, W. J (1959) Can. J. Biochem. Physiol. 37, 911-917) and separated by TLC on silica gel 60 plates (200×200 mm) in hexane/diethyl ether/acetic acid (55:45:0.5) with a final solvent migration of about 180 mm. Wax esters products were verified through the methylation of the wax ester products excised from the TLC plate (using method described in Dahlqvist et al., 2000, PNAS 97: 6487-6492) followed by the separation of the methylation products on silica gel 60 plates in hexane/diethyl ether/acetic acid (55:45:0.5). Only two components were detected, methyl esters of fatty acids and free alcohols as identified by means of appropriate standards. The amounts of wax esters produced, from the added radiolabeled sn1-palmitoyl sn2-[$^{14}$C]linoleoyl-phosphatidylcholine and the non-labelled alcohols, were quantified on the plates by electronic autoradiography (Instant Imager; Packard) as percentage of radiolabel in wax esters of total added. As shown in FIG. 3 the ATWAX was catalysing the synthesis of wax esters of 13c-docosenoyl-alcohol (○ in FIG. 3) or ricinoleoyl-alcohol (● in FIG. 3) with similar efficiencies, which reached a plateau after 4 hours of incubation at which about 55-60% of the radiolabeled acylgroups of the added phosphatidylcholine had formed a wax ester with the alcohol. Apart from the formation of the wax ester, lysophospholipids is also formed in this reaction.

The dependence of the ratio of the added lecithin and alcohol substrate on the conversion rate is presented in FIG. 4A. The conditions for the synthesis were as follows; lecithin (10 mg), sn1-oleoyl-sn2-[$^{14}$C]oleoyl-phosphatidylcholine (10 mmol; 5000 dpm/nmol) and 3.7, 7.4, 11.1, or 18,7 mg of ricinoleoyl-alcohol, giving an alcohol to lecithin ratio as indicated in FIG. 4A, dissolved in chloroform was aliquoted in 12 ml glass tubes and the chloroform was evaporated under a stream of $N_2$ (g). To the dry lipid substrate 1.2 ml of cell free medium and 60 ul 1.0 M potassium phosphate, pH 7.2 was added. The reaction mixture was sonicated in a water bath (Branson 2510) for 30 min and was further incubated at 37° C. to a final incubation of 4 hours. Lipids were extracted and analysed as described above. These analyses show that at a weight ratio of the alcohol to lecithin of 0.4 (corresponding to an equimolar amounts of alcohol and lecithin added) 28% of the radiolabeled fatty acids was converted into waxesters and by increasing the ratio 5-fold the wax ester synthesis was increased 2-fold.

Figure 4:
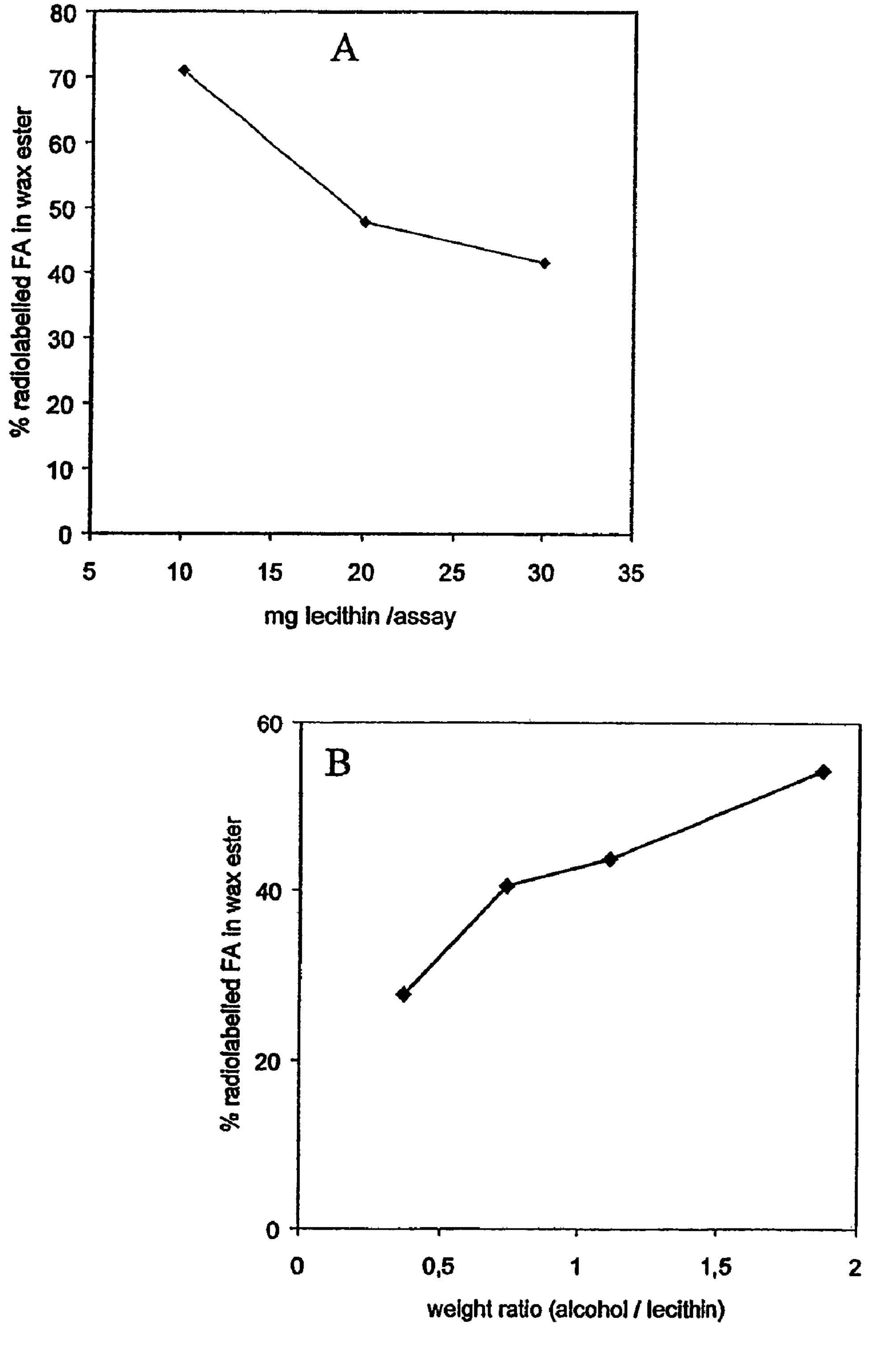
FIG. 4. shows the dependence of the ratio of the lecithin and ricinoleoyl-alcohol substrates (panel A) and increased substrate concentration with a fixed ratio of the substrates (panel B) on the wax ester synthesis were determined as described in EXAMPLE 5.

By increased substrate concentration with constant lecithin to alcohol weight ratio, the conversion into waxesters is decreased as shown in FIG. 4B. Incubating lipid substrates as described above together with 1.2 ml of cell free medium at 37° C. for 20 hours performed these analyses. From the results presented in FIG. 4 A and B it is evident that in order to optimise the yield of waxesters produced from lecithin and an alcohol the total substrate concentration and the substrate ratio are important factors to consider.

Figure 5:
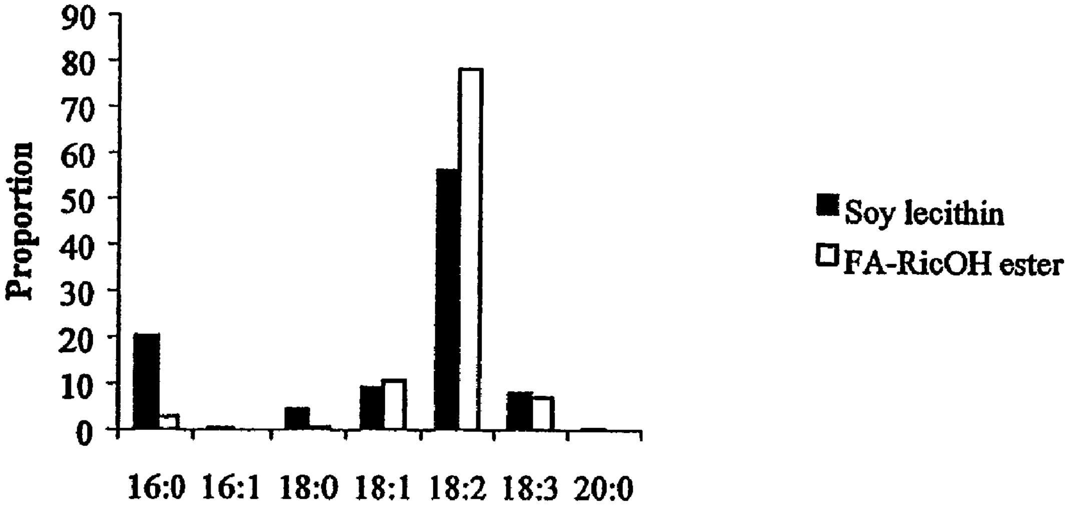
FIG. 5. shows acyl group composition of soy lecithin (filled bars) and wax esters (open bars) produced from soy lecithin and ricinoleoyl alcohol as described in EXAMPLE 5. Abbreviations used; palmitoyl (16:0), palmitoleoyl (16:1), stearoyl (18:0), oleoyl (18:1), linoleoyl (18:2), linolenoyl (18:3).

The major lipid component in the soy lecithin is phosphatidylcholine and phosphatidylethanolamine constituting about 60% of the acyl lipids present, other phospholipids present are phosphatidylinositol, phosphatidylglycerol and phosphatidic acid, which contributes up to approximately 25%, the remaining lipids are neutral lipids, lysolipids, and glycolipids. The fatty acid composition of the total lipid content of the soy lecithin used in the present study was analysed and are presented in FIG. 5 (filled bars). The major fatty acid component is linoleic acid (18:2) constituting 56% of the fatty acids present, other unsaturated fatty acids are oleic acid (18:1) and linolenic (18:3), and the unsaturated fatty acids are palmitic (16:0) and stearic acid (18:0). In FIG. 5 data are also presented on the fatty acid composition of the wax ester (open bars) produced from the soy lecithin and ricinoleoyl alcohol as described above. By comparing the fatty acid composition of the wax ester product with that of the lecithin substrate it is clear that the unsaturated fatty acids are preferentially converted into the waxesters whereas the saturated fatty acids are less efficiently used for wax ester synthesis. This can partly be explained by the fact that these unsaturated fatty acids are preferentially esterified to the sn1 position of the lipids and that ATWAX is specific for the transfer of fatty acids from the sn-2 position.

The synthesis of different waxesters from soy lecithin was achieved by using different alcohols as the acyl acceptor and with conditions as follows; lecithin (2.5 mg), sn1-oleoyl-sn2-[$^{14}$C]oleoyl-phosphatidylcholine (10 nmol; 5000 dpm/nmol) and 6 mmol of decanol, hexadecanol, 13c-docosanol, hexacosanol or ricinoleoyl-alcohol dissolved in chloroform was aliquoted in 12 ml glass tubes and the chloroform was evaporated under a stream of $N_2$ (g). To the dry lipid substrate 0.5 ml of cell free medium was added and 25 ul 1.0 M potassium phosphate, pH 7.2. The reaction mixture was sonicated in a water bath (Branson 2510) for 30 min and was further incubated at 37° C. to a final incubation of 20 hours. The synthesised wax esters were extracted and quantified as described above. The results are presented in table 1 and clearly show that apart from hexacosanol all alcohols could efficiently be used as acyl group acceptors in the synthesis of wax esters. Hexacosanol is a saturated 26 carbon alcohol with a high melting point and is therefore badly emulsified at assay conditions used in the present study and this is suggested to be the main reason to that only 5% of added radiolabeled acylgroups were esterified with the hexacosanol. In contrast, approximately 40 to 50 percent of the added radiolabeled acyl group formed wax esters with the other alcohols tested (table 1). The ricinoleic acid contains a hydroxyl group at position 12 in the carbon chain, however it could not act as an acyl acceptor in the catalyses of wax esters by the ATWAX enzyme. It is therefore concluded that in the synthesis of waxesters from lecithin and ricinoleoyl alcohol as shown in table 1 the acylgroups derived from the lecithin is exclusively esterified to the hydroxyl group of position 1 and not to that of position 12 of the ricinoleoyl alcohol.

TABLE 1

Synthesis of wax esters from sn1-oleoyl-sn2-[$^{14}$C]oleoyl-phosphatidylcholine and different alcohols (acyl acceptors) in cell free supernatants.

| Acyl acceptor | [$^{14}$C]-acylgroups in wax esters (% of added) |
|---|---|
| Butanol | Nd |
| Decanol | 42.8 |
| Hexadecanol | 44.8 |
| 13c-Docosenol | 53.9 |
| Hexacosanol | 5.1 |
| Ricinoleoyl alcohol | 51.1 |
| Ricinoleoyl fatty acid | nd |

Example 6

Figure 6:
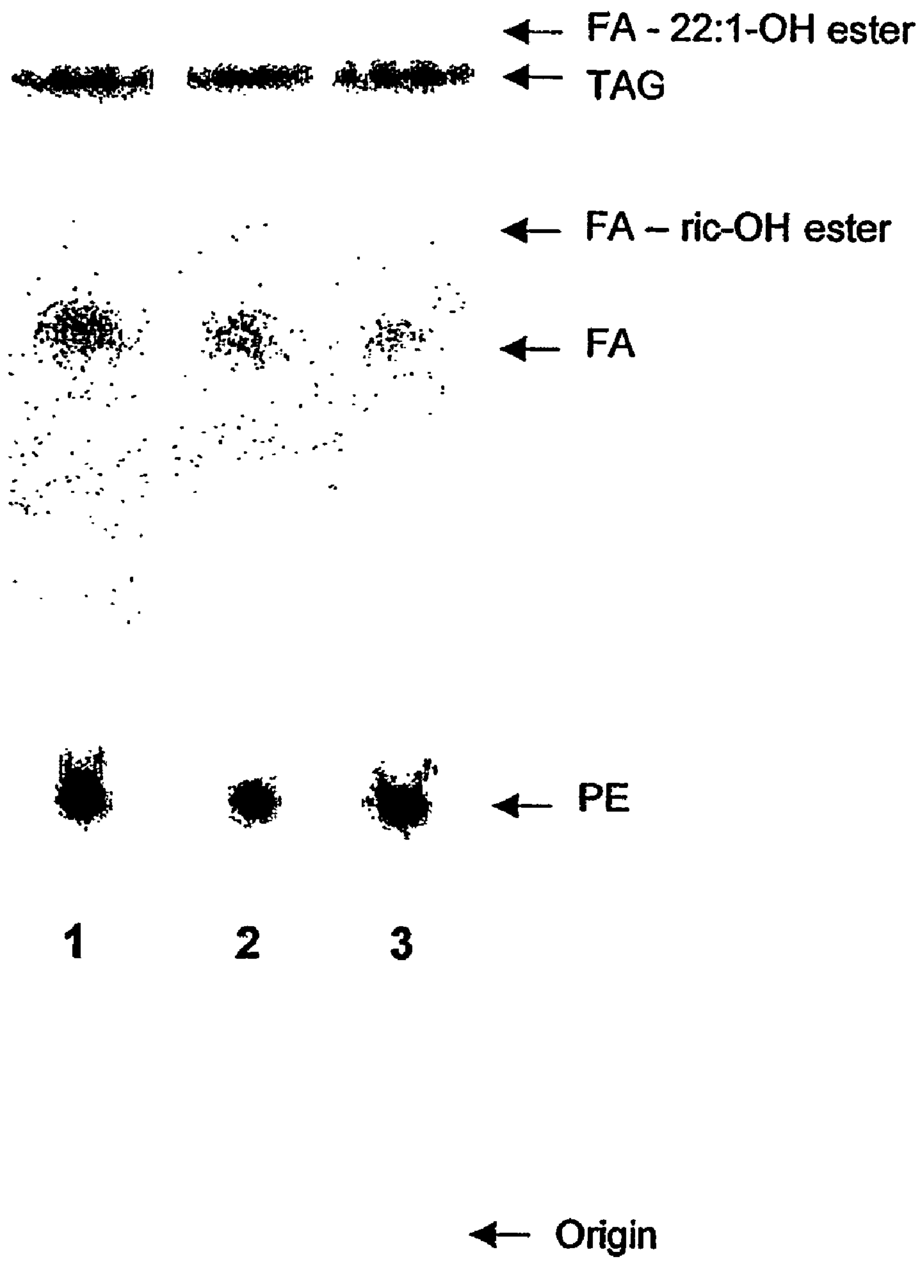
FIG. 6. shows microsomes prepared from wild type *Saccharomyces cerevisiae* cells, overexpressing the yeast PDAT gene LRO1, catalyses synthesis of triacylglycerols but not wax esters. Acyltransferase activities were analysed in the presence of the substrate sn1-oleoyl-sn2-[$^{14}$C]oleoyl-phosphatidylcholine (lane 1) together with either ricinoleoyl alcohol (Ric-OH, lane 2) or 13c-docosenol (22:1-OH, lane 3) as described in EXAMPLE 6.

The ability to catalyse the synthesis of wax ester with the membrane bound full length PDAT expressed in *Saccharomyces cerevisiae* was examined. Microsomes were prepared from wild type *S. cerevisiae* cells overexpressing the yeast PDAT gene LRO1 as described in, Dahlqvist et al., 2000 (PNAS 97:6487-6492) and were assayed for wax ester synthesis. The PDAT activity was analysed with the addition of the lipid substrates dissolved in benzene to dry aliquots of lyophilised microsomes (corresponding to 12 nmol of microsomal phosphatidylcholine) (Dahlqvist et al., 2000, PNAS 97:6487-6492). As substrate we used 2.5 nmol of sn1-oleoyl-sn2-[$^{14}$C]oleoyl-phosphatidylcholine (lane 1) together with either 2.5 nmol ricinoleoyl alcohol (Ric-OH, lane 2) or 13c-docosenol (22:1-OH, lane 3). The enzymatic assay and lipid analysis were performed as described in Dahlqvist et al., 2000 (PNAS 97:6487-6492). It is clearly shown in FIG. 6 that triacylglycerols are synthesised by an acyltransfer of the radiolabeled acyl group of the added phospholipid to the endogenous diacylglycerols present in the microsomal preparation (FIG. 6, lane 1), as previously reported. However, adding ricinoleoyl alcohol or 13c-docosenol (FIG. 6, lane 2 and 3) to the incubation formed no detectable amounts of waxesters. It is therefore concluded that the full-length membrane associated PDAT encoded by the LRO1 gene do not catalyse the wax ester synthesis such as presently shown above for the membrane independent acyltransferase, ATWAX. Hence it is here shown that the utilisation of different acyl donors and acceptors by an membrane independent acyltransferase is less limited, as compared to acyltransferases integrated into lipidmembranes via one or several membrane-spanning regions, since the accessibility of different substrates are restricted to the vicinity of the localisation of the membrane integrated enzyme.

Example 7

Genes Homologous to the *Saccharomyces cerevisiae* Gene LRO1.

Figure 7A:
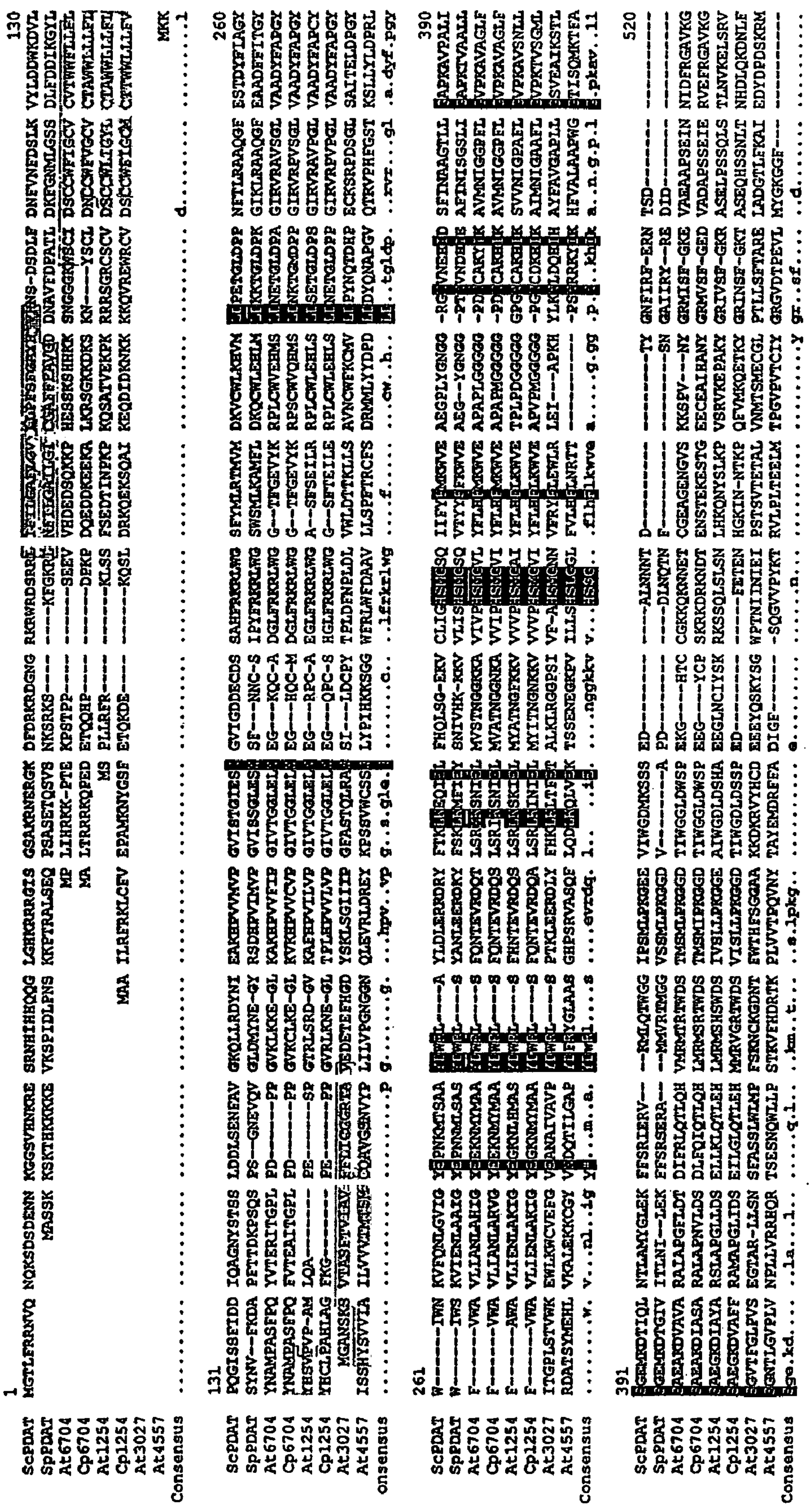
FIG. 7 shows the alignment of *Saccharomyces cerevisiae* phospholipid: diacyiglycerol acyltransferase (ScPDAT) amino acid sequence (SEQ ID NO:3), encoded from the LRO1 gene, with the Schizosaccharomyces pombe SpPDAT (SEQ ID NO: 17), Arabidopsis At67O4 (SLO TD NO:5), At1254 (SEQ ID NO:13), At3O27 (SEQ ID NO:9), At4557 (SEQ ID NO:11) and the Crepis alpina Cp67O4 (SEQ ID NO:19) and Cp1254 (SEQ ID NO:20) deduced amino acid sequences.

The yeast PDAT (ScPDAT) amino acid sequence encoded by the LRO1 gene was used to search the NCBI databases for homologous sequences in plants and microbes. In *Schizosaccharomyces pombe* one gene SpPDAT with strong homologies to the yeast PDAT gene LRO1 was identified. Four *Arabidopsis thaliana* genes At6704, At1254, At3027 and At4557 with clear homology to amino acid sequence encoded by the yeast LRO1 gene were identified. Additionally two plant genes Cp6704 and Cp1254 homologies to At6704 and At1254, respectively, were identified in *Crepis palaestina*. The full-length genes of Cp6704 and Cp1254 were amplified from double stranded cDNA, synthesised with *C. palaestina* seed mRNA as template. The coding region of the SpPDAT, At6704, At1254, At3027, At4557, Cp6704 and Cp1254 nucleic acid sequences are shown in SEQ ID NO:16, 4, 12, 8, 10, 18 and 20. The amino acid sequences encoded by SpPDAT, At6704, At1254, At3027, At4557 Cp6704 and Cp1254 sequences, i.w., SEQ ID NO:17, 5, 13, 9, 19 and 21, are aligned together with the yeast LRO1 in FIG. 7 using hierarchical clustering as described in F. Corpet, 1988, Nucl. Acids Res., 16; 10881-10890. In similarity with the yeast PDAT ScPDAT, as predicted by the THMM2.0 program (A. Krogh, B. Larsson, G. von Heijne, and E. L. L. Sonnhammer, (2001) Journal of Molecular Biology, 305:567-580), all these plant genes contains a single N terminal localised transmembrane spanning region as marked with gray boxes in FIG. 7. The full length At6704 gene has been shown to encode an enzyme with PDAT activity (Banas et al., 2003 in Advanced Research on Plant Lipids 179-182). Any data on the activity associated with the gene products of Atl254, At3027 or the At4557 has not yet been published.

Figure 8:
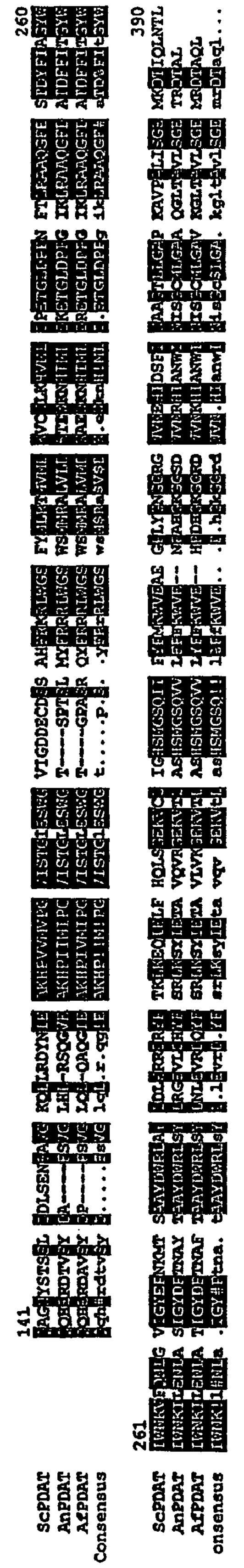
FIG. 8 shows part of the Saccharomyces cerevisiae phospholipid: diacyiglycerol acyltransferase (ScPDAT) amino acid sequence (SEQ ID NO:30), encoded from the LRO1 gene, aligned with amino acid sequences translated from the AnPDAT (SEQ ID NO:31) and AfPDAT (SEQ ID NO:32) nucleic acid sequences.

Additionally, nucleotide sequences from *Aspergillus nidulans* and *Aspergillus fumigatus* (SEQ ID NO 14 and 15) were identified. Translated amino acid sequences from these nucleotide sequences shows strong homologies with the amino acid sequence of the yeast PDAT (FIG. 8). In similarity with the yeast PDAT the *Aspergillus* sequences contains a single N-terminal membrane-spanning region, within the first 100 amino acids, as predicted by the THMM2.0 program.

Example 8

Expression of an Active Membrane Independent Acyltransferase From a Nucleotide Sequence, Derived from the Plant Gene At6704.

The yeast PDAT protein sequence was used to search the NCBI databases for homologous sequences in *Arabidopsis thaliana*. One of the identified sequences was At6704 encoding a plant PDAT (Banas et al., 2003 in Advanced Research on Plant Lipids 179-182). A cDNA clone, corresponding to At6704 was ordered from the AIMS database. The clone was sequenced and found to contain an insertion of one base. This extra base was deleted through site directed mutagenesis. The At6704 gene encodes a plant-PDAT with a membrane-spanning region from aa 48 to aa 70 as predicted by the THMM2.0 program (A. Krogh, B. Larsson, G. von Heijne, and E. L. L. Sonnhammer, (2001) Journal of Molecular Biology, 305:567-580).

A nucleotide sequence, SEQ ID NO: 6 identical in sequence to the part of the plant PDAT gene At6704 encoding the amino acid residues 74 to 671 (SEQ ID NO: 7) was amplified by thermo stable Pfu Turbo Polymerase (Stratagene Inc.) from the plasmid template pUS56 containing the full length At6704 plant gene. The forward (5' end) primer used for this PCR reaction was; 5'CCATGGGAATGAATTCGCAATGCCTGCGAGCTTCCCTCAGTATGTA3' (SEQ ID NO: 28) The oligonucleotide sequence; 5'GAATTCGTTAGCGGCCGCCAGCTTCAGGTCAATACGCTCCGACCA3' (SEQ ID NO: 29) was used as the reverse (3' end) primer in the PCR amplification. The amino acid sequence (SEQ ID NO:7) encoded by the amplified nucleotide sequence (SEQ ID NO:6) lacks the amino acid residues 1 to amino acid 73 including the transmembrane region of amino acid residues 48 to 70 present in the plant PDAT as predicted by the THMM2.0 program.

The amplified PCR product above, was purified, digested by EcoRI and NotI, and subcloned between the EcoRI and NotI sites of the *Pichia* expression vector PpicZαA in frame with the N-terminal sequence encoding the αfactor signalpeptide present in the expression vector and a C-terminal c-myc epitope followed by a polyhistidine tag. The resultant *Pichia* expression vectors are named pHisATWAX-P6. The vector was linearized using unique SacI restriction site for transformation into *Pichia pastoris* host strain KM71H. Transformants were cultivated for the expression of the transformed gene as described in EXAMPLE 2. To determine the enzyme activity in the cell free culture medium the cell free supernatant was assayed for enzyme activity as follows. The cell free supernatant of the induced cultures of KM71H transformed with pHisATWAX as described in EXAMPLE 2, from 116 hours of growth of *Pichia pastoris* KM71H transformed with the pHisATWAX-P6 secreting, the polypeptide HisATWAX-P6 (FIG. 9, lane 1 and 2), the congenic wt strain (FIG. 9, lane 3 and 4) and KM71H expressing the polypeptide ATWAX were assayed for acyl transferase activity.

Figure 9:
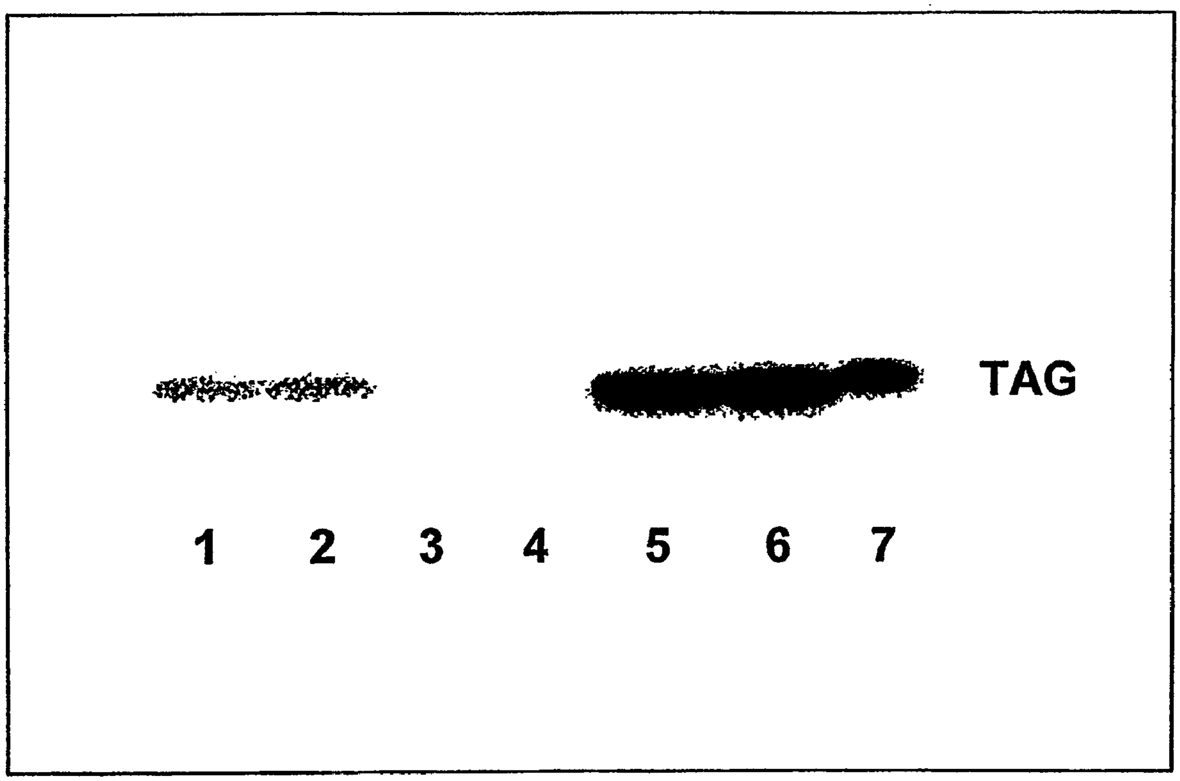
FIG. 9. shows the synthesis of triacylglycerol catalysed by the membrane independent acyltransferase (HisATWAX-P6), as visualized by autoradiography of lipid products separated on TLC.

.Lipid substrate, sn1-palmitoyl sn2-[$^{14}$C]linoleoyl-phosphatidylethanolamine (5 nmol; 5000 dpm/nmol) and dioleoylglycerol (2.5 nmol) dissolved in chloroform was aliquoted in 1.5 ml tubes and the chloroform was evaporated under a stream of $N_2$ (g). After addition of 20 ul 0.25 M potassium phosphate, pH 7.2, the mixture was violently agitated and 80 ul of cell free supernatant was added and incubated at 30° C. for 90 min. Lipids were extracted from the reaction mixture into chloroform (Bligh, E. G. and Dyer, W. J (1959) Can. J. Biochem. Physiol. 37, 911-917) and separated by TLC on silica gel 60 plates (200×200 mm) in chloroform/methanol/acetic acid/water (85:15:10:3.5) migrating 90 mm using an automatic developing chamber (Camag). The plate was dried and redeveloped in hexane/diethyl ether/acetic acid (80:20:1) with a solvent migration of 180 mm. The radioactive lipids were visualized and quantified on the plates by electronic autoradiography (Instant Imager; Packard). As a control, the enzyme activity in the cell free supernatant of the wild type host strain culture was analysed. As shown in FIG. 9, radiolabeled triacylglycerol (TAG) is formed, from the added lipid substrate, sn1-palmitoyl sn2-[$^{14}$C]linoleoyl-phosphatidylethanolamine and dioleoylglycerol, in cell free extract of *Pichia* strain transformed with pHisATWAX-P6. This demonstrates that the truncated membrane independent form of the plant PDAT, referred to as a membrane independent acyltransferase that we have named HisATWAX-P6, is able of catalysing the formation of TAG by an acyltransfer from phosphatidylethanolamine to diacylglycerol (DAG).

The invention claimed is:

1. An isolated polypeptide obtained from a polypeptide comprising the amino acid sequence set forth in SEQ ID NO:3, wherein said polypeptide comprising the amino acid sequence set forth in SEQ ID NO:3 is an integral membrane protein comprising a membrane spanning region, wherein amino acid residues 1 to 97 have been deleted from the N-terminus as compared to the amino acid sequence set forth in SEQ ID NO:3, and wherein the polypeptide has membrane independent acyltransferase activity.

2. The polypeptide according to claim 1 ,wherein the polypeptide is an acyltransferase active at a pH range of from about 4 to about 10 and stable at a temperature below 60° C.

3. The polypeptide according to claim 2, wherein the polypeptide is an acyltransferase active at a pH of 7.2 at a temperature of about 30° C.

4. The polypeptide according to claim 1, wherein the polypeptide is immobilized to a carrier.

5. The polypeptide according to claim 1, wherein the polypeptide is lyophilized and/or freeze-dried.

6. A kit comprising the polypeptide according to claim 1 and a stabilizer.

7. The kit according to claim 6, wherein the polypeptide is in a lyophilized form or freeze-dried.

8. A kit according to claim 6, wherein the polypeptide is immobilized to a carrier.

9. A detergent composition comprising the polypeptide of claim 1.

10. A food composition comprising the polypeptide of claim 1.

11. A method for removal of a phospholipid from vegetable oil, comprising contacting the vegetable oil with the polypeptide of claim 1, wherein fatty acids are transferred from said phospholipid to an acceptor molecule present in said vegetable oil.

12. A method according to claim 11, wherein said phospholipid is lecithin, wherein said lecithin is converted to lysolecithin, and wherein said lysolecithin is removed from the oil into a water phase.

13. A polypeptide according to claim 1, wherein said membrane independent acyltransferase activity comprises ester synthesis.

14. A polypeptide according to claim 13, wherein said ester synthesis comprises wax ester synthesis.

15. A method for preparing a baked product from a dough comprising converting polar lipids in a flour into lysolipids, said method comprising contacting a dough comprising said flour with a polypeptide according to claim 1 to said dough, wherein polar lipids in said flour are enzymatically converted into lysolipids by said polypeptide, thereby preparing the baked product.

16. A method for converting lecithin or phospholipids to lysolecithin or lysophospholipids in a food material, comprising contacting said food material with a polypeptide according to claim 1.

17. A method according to claim 16, wherein said food material is selected from the group consisting of milk, flour, eggs, soy protein, and cocoa.

* * * * *

SEQUENCE LISTING

<160> NUMBER OF SEQ ID NOS: 21

<210> SEQ ID NO 1
<211> LENGTH: 1986
<212> TYPE: DNA
<213> ORGANISM: Saccharomyces cerevisiae

<400> SEQUENCE: 1

```
atgggcacac tgtttcgaag aaatgtccag aaccaaaaga gtgattctga tgaaaacaat     60
aaagggggtt ctgttcataa caagcgagag agcagaaacc acattcatca tcaacaggga    120
ttaggccata agagaagaag gggtattagt ggcagtgcaa aaagaaatga gcgtggcaaa    180
gatttcgaca ggaaaagaga cgggaacggt agaaaacgtt ggagagattc cagaagactg    240
attttcattc ttggtgcatt cttaggtgta cttttgccgt ttagctttgg cgcttatcat    300
gttcataata gcgatagcga cttgtttgac aactttgtaa attttgattc acttaaagtg    360
tatttggatg attggaaaga tgttctccca caaggtataa gttcgtttat tgatgatatt    420
caggctggta actactccac atcttcttta gatgatctca gtgaaaattt tgccgttggt    480
aaacaactct tacgtgatta taatatcgag gccaaacatc ctgttgtaat ggttcctggt    540
gtcatttcta cgggaattga aagctgggga gttattggag acgatgagtg cgatagttct    600
gcgcattttc gtaaacggct gtggggaagt ttttacatgc tgagaacaat ggttatggat    660
aaagtttgtt ggttgaaaca tgtaatgtta gatcctgaaa caggtctgga cccaccgaac    720
tttacgctac gtgcagcaca gggcttcgaa tcaactgatt atttcatcgc agggtattgg    780
atttggaaca aagttttcca aaatctggga gtaattggct atgaacccaa taaaatgacg    840
agtgctgcgt atgattggag gcttgcatat ttagatctag aaagacgcga taggtacttt    900
acgaagctaa aggaacaaat cgaactgttt catcaattga gtggtgaaaa agtttgttta    960
attggacatt ctatgggttc tcagattatc ttttacttta tgaaatgggt cgaggctgaa   1020
ggccctcttt acggtaatgg tggtcgtggc tgggttaacg aacacataga ttcattcatt   1080
aatgcagcag ggacgcttct gggcgctcca aaggcagttc cagctctaat tagtggtgaa   1140
atgaaagata ccattcaatt aaatacgtta gccatgtatg gtttggaaaa gttcttctca   1200
agaattgaga gagtaaaaat gttacaaacg tggggtggta taccatcaat gctaccaaag   1260
ggagaagagg tcatttgggg ggatatgaag tcatcttcag aggatgcatt gaataacaac   1320
actgacacat acggcaattt cattcgattt gaaaggaata cgagcgatgc tttcaacaaa   1380
aatttgacaa tgaaagacgc cattaacatg acattatcga tatcacctga atggctccaa   1440
agaagagtac atgagcagta ctcgttcggc tattccaaga atgaagaaga gttaagaaaa   1500
aatgagctac accacaagca ctggtcgaat ccaatggaag taccacttcc agaagctccc   1560
cacatgaaaa tctattgtat atacggggtg aacaacccaa ctgaaagggc atatgtatat   1620
aaggaagagg atgactcctc tgctctgaat ttgaccatcg actacgaaag caagcaacct   1680
gtattcctca ccgaggggga cggaaccgtt ccgctcgtgg cgcattcaat gtgtcacaaa   1740
tgggcccagg gtgcttcacc gtacaaccct gccggaatta acgttactat tgtggaaatg   1800
aaacaccagc cagatcgatt tgatatacgt ggtggagcaa aaagcgccga acacgtagac   1860
atcctcggca gcgcggagtt gaacgattac atcttgaaaa ttgcaagcgg taatggcgat   1920
ctcgtcgagc cacgccaatt gtctaatttg agccagtggg tttctcagat gcccttccca   1980
atgtaa                                                               1986
```

-continued

<210> SEQ ID NO 2
<211> LENGTH: 1701
<212> TYPE: DNA
<213> ORGANISM: Saccharomyces cerevisiae

<400> SEQUENCE: 2

```
gaattcgctt atcatgttca taatagcgat agcgacttgt ttgacaactt tgtaaatttt     60

gattcactta aagtgtattt ggatgattgg aaagatgttc tcccacaagg tataagttcg    120

tttattgatg atattcaggc tggtaactac tccacatctt ctttagatga tctcagtgaa    180

aattttgccg ttggtaaaca actcttacgt gattataata tcgaggccaa acatcctgtt    240

gtaatggttc ctggtgtcat ttctacggga attgaaagct ggggagttat tggagacgat    300

gagtgcgata gttctgcgca ttttcgtaaa cggctgtggg gaagttttta catgctgaga    360

acaatggtta tggataaagt ttgttggttg aaacatgtaa tgttagatcc tgaaacaggt    420

ctggacccac cgaactttac gctacgtgca gcacagggct tcgaatcaac tgattatttc    480

atcgcagggt attggatttg gaacaaagtt ttccaaaatc tgggagtaat tggctatgaa    540

cccaataaaa tgacgagtgc tgcgtatgat tggaggcttg catatttaga tctagaaaga    600

cgcgataggt actttacgaa gctaaaggaa caaatcgaac tgtttcatca attgagtggt    660

gaaaaagttt gtttaattgg acattctatg ggttctcaga ttatctttta ctttatgaaa    720

tgggtcgagg ctgaaggccc tctttacggt aatggtggtc gtggctgggt taacgaacac    780

atagattcat tcattaatgc agcagggacg cttctgggcg ctccaaaggc agttccagct    840

ctaattagtg gtgaaatgaa agataccatt caattaaata cgttagccat gtatggtttg    900

gaaaagttct tctcaagaat tgagagagta aaaatgttac aaacgtgggg tggtatacca    960

tcaatgctac caaagggaga agaggtcatt tggggggata tgaagtcatc ttcagaggat   1020

gcattgaata acaacactga cacatacggc aatttcattc gatttgaaag gaatacgagc   1080

gatgctttca acaaaaattt gacaatgaaa gacgccatta acatgacatt atcgatatca   1140

cctgaatggc tccaaagaag agtacatgag cagtactcgt tcggctattc caagaatgaa   1200

gaagagttaa gaaaaaatga gctacaccac aagcactggt cgaatccaat ggaagtacca   1260

cttccagaag ctccccacat gaaaatctat tgtatatacg ggtgaacaa cccaactgaa    1320

agggcatatg tatataagga agaggatgac tcctctgctc tgaatttgac catcgactac   1380

gaaagcaagc aacctgtatt cctcaccgag ggggacggaa ccgttccgct cgtggcgcat   1440

tcaatgtgtc acaaatgggc ccagggtgct tcaccgtaca accctgccgg aattaacgtt   1500

actattgtgg aaatgaaaca ccagccagat cgatttgata tacgtggtgg agcaaaaagc   1560

gccgaacacg tagacatcct cggcagcgcg gagttgaacg attacatctt gaaaattgca   1620

agcggtaatg gcgatctcgt cgagccacgc caattgtcta atttgagcca gtgggtttct   1680

cagatgccct tcccaatgtg a                                             1701
```

<210> SEQ ID NO 3
<211> LENGTH: 661
<212> TYPE: PRT
<213> ORGANISM: Saccharomyces cerevisiae

<400> SEQUENCE: 3

```
Met Gly Thr Leu Phe Arg Arg Asn Val Gln Asn Gln Lys Ser Asp Ser
1               5                   10                  15

Asp Glu Asn Asn Lys Gly Gly Ser Val His Asn Lys Arg Glu Ser Arg
```

-continued

```
            20                  25                  30

Asn His Ile His His Gln Gln Gly Leu Gly His Lys Arg Arg Arg Gly
        35                  40                  45

Ile Ser Gly Ser Ala Lys Arg Asn Glu Arg Gly Lys Asp Phe Asp Arg
    50                  55                  60

Lys Arg Asp Gly Asn Gly Arg Lys Arg Trp Arg Asp Ser Arg Arg Leu
65                  70                  75                  80

Ile Phe Ile Leu Gly Ala Phe Leu Gly Val Leu Leu Pro Phe Ser Phe
                85                  90                  95

Gly Ala Tyr His Val His Asn Ser Asp Ser Asp Leu Phe Asp Asn Phe
            100                 105                 110

Val Asn Phe Asp Ser Leu Lys Val Tyr Leu Asp Asp Trp Lys Asp Val
        115                 120                 125

Leu Pro Gln Gly Ile Ser Ser Phe Ile Asp Asp Ile Gln Ala Gly Asn
    130                 135                 140

Tyr Ser Thr Ser Ser Leu Asp Asp Leu Ser Glu Asn Phe Ala Val Gly
145                 150                 155                 160

Lys Gln Leu Leu Arg Asp Tyr Asn Ile Glu Ala Lys His Pro Val Val
                165                 170                 175

Met Val Pro Gly Val Ile Ser Thr Gly Ile Glu Ser Trp Gly Val Ile
            180                 185                 190

Gly Asp Asp Glu Cys Asp Ser Ser Ala His Phe Arg Lys Arg Leu Trp
        195                 200                 205

Gly Ser Phe Tyr Met Leu Arg Thr Met Val Met Asp Lys Val Cys Trp
    210                 215                 220

Leu Lys His Val Met Leu Asp Pro Glu Thr Gly Leu Asp Pro Pro Asn
225                 230                 235                 240

Phe Thr Leu Arg Ala Ala Gln Gly Phe Glu Ser Thr Asp Tyr Phe Ile
                245                 250                 255

Ala Gly Tyr Trp Ile Trp Asn Lys Val Phe Gln Asn Leu Gly Val Ile
            260                 265                 270

Gly Tyr Glu Pro Asn Lys Met Thr Ser Ala Ala Tyr Asp Trp Arg Leu
        275                 280                 285

Ala Tyr Leu Asp Leu Glu Arg Arg Asp Arg Tyr Phe Thr Lys Leu Lys
    290                 295                 300

Glu Gln Ile Glu Leu Phe His Gln Leu Ser Gly Glu Lys Val Cys Leu
305                 310                 315                 320

Ile Gly His Ser Met Gly Ser Gln Ile Ile Phe Tyr Phe Met Lys Trp
                325                 330                 335

Val Glu Ala Glu Gly Pro Leu Tyr Gly Asn Gly Gly Arg Gly Trp Val
            340                 345                 350

Asn Glu His Ile Asp Ser Phe Ile Asn Ala Ala Gly Thr Leu Leu Gly
        355                 360                 365

Ala Pro Lys Ala Val Pro Ala Leu Ile Ser Gly Glu Met Lys Asp Thr
    370                 375                 380

Ile Gln Leu Asn Thr Leu Ala Met Tyr Gly Leu Glu Lys Phe Phe Ser
385                 390                 395                 400

Arg Ile Glu Arg Val Lys Met Leu Gln Thr Trp Gly Gly Ile Pro Ser
                405                 410                 415

Met Leu Pro Lys Gly Glu Glu Val Ile Trp Gly Asp Met Lys Ser Ser
            420                 425                 430

Ser Glu Asp Ala Leu Asn Asn Asn Thr Asp Thr Tyr Gly Asn Phe Ile
        435                 440                 445
```

-continued

```
Arg Phe Glu Arg Asn Thr Ser Asp Ala Phe Asn Lys Asn Leu Thr Met
    450                 455                 460

Lys Asp Ala Ile Asn Met Thr Leu Ser Ile Ser Pro Glu Trp Leu Gln
465                 470                 475                 480

Arg Arg Val His Glu Gln Tyr Ser Phe Gly Tyr Ser Lys Asn Glu Glu
                485                 490                 495

Glu Leu Arg Lys Asn Glu Leu His His Lys His Trp Ser Asn Pro Met
            500                 505                 510

Glu Val Pro Leu Pro Glu Ala Pro His Met Lys Ile Tyr Cys Ile Tyr
        515                 520                 525

Gly Val Asn Asn Pro Thr Glu Arg Ala Tyr Val Tyr Lys Glu Glu Asp
    530                 535                 540

Asp Ser Ser Ala Leu Asn Leu Thr Ile Asp Tyr Glu Ser Lys Gln Pro
545                 550                 555                 560

Val Phe Leu Thr Glu Gly Asp Gly Thr Val Pro Leu Val Ala His Ser
                565                 570                 575

Met Cys His Lys Trp Ala Gln Gly Ala Ser Pro Tyr Asn Pro Ala Gly
            580                 585                 590

Ile Asn Val Thr Ile Val Glu Met Lys His Gln Pro Asp Arg Phe Asp
        595                 600                 605

Ile Arg Gly Gly Ala Lys Ser Ala Glu His Val Asp Ile Leu Gly Ser
    610                 615                 620

Ala Glu Leu Asn Asp Tyr Ile Leu Lys Ile Ala Ser Gly Asn Gly Asp
625                 630                 635                 640

Leu Val Glu Pro Arg Gln Leu Ser Asn Leu Ser Gln Trp Val Ser Gln
                645                 650                 655

Met Pro Phe Pro Met
            660
```

<210> SEQ ID NO 4
<211> LENGTH: 2016
<212> TYPE: DNA
<213> ORGANISM: Arabidopsis thaliana

<400> SEQUENCE: 4

```
atgcccctta ttcatcggaa aaagccgacg gagaaaccat cgacgccgcc atctgaagag     60

gtggtgcacg atgaggattc gcaaaagaaa ccacacgaat cttccaaatc ccaccataag    120

aaatcgaacg gaggagggaa gtggtcgtgc atcgattctt gttgttggtt cattgggtgt    180

gtgtgtgtaa cctggtggtt tcttctcttc ctttacaacg caatgcctgc gagcttccct    240

cagtatgtaa cggagcgaat cacgggtcct ttgcctgacc cgcccggtgt taagctcaaa    300

aaagaaggtc ttaaggcgaa acatcctgtt gtcttcattc ctgggattgt caccggtggg    360

ctcgagcttt gggaaggcaa acaatgcgct gatggtttat ttagaaaacg tttgtggggt    420

ggaacttttg gtgaagtcta caaaaggcct ctatgttggg tggaacacat gtcacttgac    480

aatgaaactg ggttggatcc agctggtatt agagttcgag ctgtatcagg actcgtggct    540

gctgactact ttgctcctgg ctactttgtc tgggcagtgc tgattgctaa ccttgcacat    600

attggatatg aagagaaaaa tatgtacatg gctgcatatg actggcggct ttcgtttcag    660

aacacagagg tacgtgatca gactcttagc cgtatgaaaa gtaatataga gttgatggtt    720

tctaccaacg gtggaaaaaa agcagttata gttccgcatt ccatgggggt cttgtatttt    780

ctacatttta tgaagtgggt tgaggcacca gctcctctgg gtggcggggg tgggccagat    840
```

-continued

```
tggtgtgcaa agtatattaa ggcggtgatg aacattggtg gaccatttct tggtgttcca    900

aaagctgttg cagggctttt ctctgctgaa gcaaaggatg ttgcagttgc cagagcgatt    960

gccccaggat tcttagacac cgatatattt agacttcaga ccttgcagca tgtaatgaga   1020

atgacacgca catgggactc aacaatgtct atgttaccga agggaggtga cacgatatgg   1080

ggcgggcttg attggtcacc ggagaaaggc cacacctgtt gtgggaaaaa gcaaaagaac   1140

aacgaaactt gtggtgaagc aggtgaaaac ggagtttcca agaaaagtcc tgttaactat   1200

ggaaggatga tatcttttgg gaaagaagta gcagaggctg cgccatctga gattaataat   1260

attgattttc gaggtgctgt caaaggtcag agtatcccaa atcacacctg tcgtgacgtg   1320

tggacagagt accatgacat gggaattgct gggatcaaag ctatcgctga gtataaggtc   1380

tacactgctg gtgaagctat agatctacta cattatgttg ctcctaagat gatggcgcgt   1440

ggtgccgctc atttctctta tggaattgct gatgatttgg atgacaccaa gtatcaagat   1500

cccaaatact ggtcaaatcc gttagagaca aaattaccga atgctcctga gatggaaatc   1560

tactcattat acggagtggg gataccaacg gaacgagcat acgtatacaa gcttaaccag   1620

tctcccgaca gttgcatccc ctttcagata ttcacttctg ctcacgagga ggacgaagat   1680

agctgtctga aagcaggagt ttacaatgtg gatggggatg aaacagtacc cgtcctaagt   1740

gccgggtaca tgtgtgcaaa agcgtggcgt ggcaagacaa gattcaaccc ttccggaatc   1800

aagacttata taagagaata caatcactct ccgccggcta acctgttgga agggcgcggg   1860

acgcagagtg gtgcccatgt tgatatcatg ggaaactttg ctttgatcga agatatcatg   1920

agggttgccg ccggaggtaa cggtctgat ataggacatg accaggtcca ctctggcata   1980

tttgaatggt cggagcgtat tgacctgaag ctgtga                             2016
```

<210> SEQ ID NO 5
<211> LENGTH: 671
<212> TYPE: PRT
<213> ORGANISM: Arabidopsis thaliana

<400> SEQUENCE: 5

```
Met Pro Leu Ile His Arg Lys Lys Pro Thr Glu Lys Pro Ser Thr Pro
1               5                   10                  15

Pro Ser Glu Glu Val Val His Asp Glu Asp Ser Gln Lys Lys Pro His
            20                  25                  30

Glu Ser Ser Lys Ser His His Lys Lys Ser Asn Gly Gly Gly Lys Trp
        35                  40                  45

Ser Cys Ile Asp Ser Cys Cys Trp Phe Ile Gly Cys Val Cys Val Thr
    50                  55                  60

Trp Trp Phe Leu Leu Phe Leu Tyr Asn Ala Met Pro Ala Ser Phe Pro
65                  70                  75                  80

Gln Tyr Val Thr Glu Arg Ile Thr Gly Pro Leu Pro Asp Pro Pro Gly
                85                  90                  95

Val Lys Leu Lys Lys Glu Gly Leu Lys Ala Lys His Pro Val Val Phe
            100                 105                 110

Ile Pro Gly Ile Val Thr Gly Gly Leu Glu Leu Trp Glu Gly Lys Gln
        115                 120                 125

Cys Ala Asp Gly Leu Phe Arg Lys Arg Leu Trp Gly Gly Thr Phe Gly
    130                 135                 140

Glu Val Tyr Lys Arg Pro Leu Cys Trp Val Glu His Met Ser Leu Asp
145                 150                 155                 160

Asn Glu Thr Gly Leu Asp Pro Ala Gly Ile Arg Val Arg Ala Val Ser
```

-continued

```
                165                 170                 175

Gly Leu Val Ala Ala Asp Tyr Phe Ala Pro Gly Tyr Phe Val Trp Ala
            180                 185                 190

Val Leu Ile Ala Asn Leu Ala His Ile Gly Tyr Glu Glu Lys Asn Met
        195                 200                 205

Tyr Met Ala Ala Tyr Asp Trp Arg Leu Ser Phe Gln Asn Thr Glu Val
    210                 215                 220

Arg Asp Gln Thr Leu Ser Arg Met Lys Ser Asn Ile Glu Leu Met Val
225                 230                 235                 240

Ser Thr Asn Gly Gly Lys Lys Ala Val Ile Val Pro His Ser Met Gly
                245                 250                 255

Val Leu Tyr Phe Leu His Phe Met Lys Trp Val Glu Ala Pro Ala Pro
            260                 265                 270

Leu Gly Gly Gly Gly Gly Pro Asp Trp Cys Ala Lys Tyr Ile Lys Ala
        275                 280                 285

Val Met Asn Ile Gly Gly Pro Phe Leu Gly Val Pro Lys Ala Val Ala
    290                 295                 300

Gly Leu Phe Ser Ala Glu Ala Lys Asp Val Ala Val Ala Arg Ala Ile
305                 310                 315                 320

Ala Pro Gly Phe Leu Asp Thr Asp Ile Phe Arg Leu Gln Thr Leu Gln
                325                 330                 335

His Val Met Arg Met Thr Arg Thr Trp Asp Ser Thr Met Ser Met Leu
            340                 345                 350

Pro Lys Gly Gly Asp Thr Ile Trp Gly Gly Leu Asp Trp Ser Pro Glu
        355                 360                 365

Lys Gly His Thr Cys Cys Gly Lys Lys Gln Lys Asn Asn Glu Thr Cys
    370                 375                 380

Gly Glu Ala Gly Glu Asn Gly Val Ser Lys Lys Ser Pro Val Asn Tyr
385                 390                 395                 400

Gly Arg Met Ile Ser Phe Gly Lys Glu Val Ala Glu Ala Ala Pro Ser
                405                 410                 415

Glu Ile Asn Asn Ile Asp Phe Arg Gly Ala Val Lys Gly Gln Ser Ile
            420                 425                 430

Pro Asn His Thr Cys Arg Asp Val Trp Thr Glu Tyr His Asp Met Gly
        435                 440                 445

Ile Ala Gly Ile Lys Ala Ile Ala Glu Tyr Lys Val Tyr Thr Ala Gly
    450                 455                 460

Glu Ala Ile Asp Leu Leu His Tyr Val Ala Pro Lys Met Met Ala Arg
465                 470                 475                 480

Gly Ala Ala His Phe Ser Tyr Gly Ile Ala Asp Asp Leu Asp Asp Thr
                485                 490                 495

Lys Tyr Gln Asp Pro Lys Tyr Trp Ser Asn Pro Leu Glu Thr Lys Leu
            500                 505                 510

Pro Asn Ala Pro Glu Met Glu Ile Tyr Ser Leu Tyr Gly Val Gly Ile
        515                 520                 525

Pro Thr Glu Arg Ala Tyr Val Tyr Lys Leu Asn Gln Ser Pro Asp Ser
    530                 535                 540

Cys Ile Pro Phe Gln Ile Phe Thr Ser Ala His Glu Glu Asp Glu Asp
545                 550                 555                 560

Ser Cys Leu Lys Ala Gly Val Tyr Asn Val Asp Gly Asp Glu Thr Val
                565                 570                 575

Pro Val Leu Ser Ala Gly Tyr Met Cys Ala Lys Ala Trp Arg Gly Lys
            580                 585                 590
```

-continued

```
Thr Arg Phe Asn Pro Ser Gly Ile Lys Thr Tyr Ile Arg Glu Tyr Asn
        595                 600                 605

His Ser Pro Pro Ala Asn Leu Leu Glu Gly Arg Gly Thr Gln Ser Gly
    610                 615                 620

Ala His Val Asp Ile Met Gly Asn Phe Ala Leu Ile Glu Asp Ile Met
625                 630                 635                 640

Arg Val Ala Ala Gly Gly Asn Gly Ser Asp Ile Gly His Asp Gln Val
                645                 650                 655

His Ser Gly Ile Phe Glu Trp Ser Glu Arg Ile Asp Leu Lys Leu
            660                 665                 670


<210> SEQ ID NO 6
<211> LENGTH: 1803
<212> TYPE: DNA
<213> ORGANISM: Arabidopsis thaliana

<400> SEQUENCE: 6

gaattcgcaa tgcctgcgag cttccctcag tatgtaacgg agcgaatcac gggtcctttg     60

cctgacccgc ccggtgttaa gctcaaaaaa gaaggtctta aggcgaaaca tcctgttgtc    120

ttcattcctg ggattgtcac cggtgggctc gagctttggg aaggcaaaca atgcgctgat    180

ggtttattta gaaaacgttt gtggggtgga acttttggtg aagtctacaa aaggcctcta    240

tgttgggtgg aacacatgtc acttgacaat gaaactgggt tggatccagc tggtattaga    300

gttcgagctg tatcaggact cgtggctgct gactactttg ctcctggcta ctttgtctgg    360

gcagtgctga ttgctaacct tgcacatatt ggatatgaag agaaaaatat gtacatggct    420

gcatatgact ggcggctttc gtttcagaac acagaggtac gtgatcagac tcttagccgt    480

atgaaaagta atatagagtt gatggtttct accaacggtg gaaaaaaagc agttatagtt    540

ccgcattcca tgggggtctt gtattttcta cattttatga agtgggttga ggcaccagct    600

cctctgggtg gcgggggtgg gccagattgg tgtgcaaagt atattaaggc ggtgatgaac    660

attggtggac catttcttgg tgttccaaaa gctgttgcag ggcttttctc tgctgaagca    720

aaggatgttg cagttgccag agcgattgcc ccaggattct tagacaccga tatatttaga    780

cttcagacct tgcagcatgt aatgagaatg acacgcacat gggactcaac aatgtctatg    840

ttaccgaagg gaggtgacac gatatggggc gggcttgatt ggtcaccgga gaaaggccac    900

acctgttgtg ggaaaaagca aaagaacaac gaaacttgtg gtgaagcagg tgaaaacgga    960

gtttccaaga aaagtcctgt taactatgga aggatgatat cttttgggaa agaagtagca   1020

gaggctgcgc catctgagat taataatatt gattttcgag gtgctgtcaa aggtcagagt   1080

atcccaaatc acacctgtcg tgacgtgtgg acagagtacc atgacatggg aattgctggg   1140

atcaaagcta tcgctgagta taaggtctac actgctggtg aagctataga tctactacat   1200

tatgttgctc ctaagatgat ggcgcgtggt gccgctcatt tctcttatgg aattgctgat   1260

gatttggatg acaccaagta tcaagatccc aaatactggt caaatccgtt agagacaaaa   1320

ttaccgaatg ctcctgagat ggaaatctac tcattatacg gagtggggat accaacggaa   1380

cgagcatacg tatacaagct taaccagtct cccgacagtt gcatcccctt tcagatattc   1440

acttctgctc acgaggagga cgaagatagc tgtctgaaag caggagttta caatgtggat   1500

ggggatgaaa cagtacccgt cctaagtgcc gggtacatgt gtgcaaaagc gtggcgtggc   1560

aagacaagat tcaacccttc cggaatcaag acttatataa gagaatacaa tcactctccg   1620

ccggctaacc tgttggaagg gcgcgggacg cagagtggtg cccatgttga tatcatggga   1680
```

-continued

```
aactttgctt tgatcgaaga tatcatgagg gttgccgccg gaggtaacgg gtctgatata   1740

ggacatgacc aggtccactc tggcatattt gaatggtcgg agcgtattga cctgaagctg   1800

tga                                                                 1803


<210> SEQ ID NO 7
<211> LENGTH: 600
<212> TYPE: PRT
<213> ORGANISM: Arabidopsis thaliana

<400> SEQUENCE: 7

Glu Phe Ala Met Pro Ala Ser Phe Pro Gln Tyr Val Thr Glu Arg Ile
1               5                   10                  15

Thr Gly Pro Leu Pro Asp Pro Pro Gly Val Lys Leu Lys Lys Glu Gly
            20                  25                  30

Leu Lys Ala Lys His Pro Val Val Phe Ile Pro Gly Ile Val Thr Gly
        35                  40                  45

Gly Leu Glu Leu Trp Glu Gly Lys Gln Cys Ala Asp Gly Leu Phe Arg
    50                  55                  60

Lys Arg Leu Trp Gly Gly Thr Phe Gly Glu Val Tyr Lys Arg Pro Leu
65                  70                  75                  80

Cys Trp Val Glu His Met Ser Leu Asp Asn Glu Thr Gly Leu Asp Pro
                85                  90                  95

Ala Gly Ile Arg Val Arg Ala Val Ser Gly Leu Val Ala Ala Asp Tyr
            100                 105                 110

Phe Ala Pro Gly Tyr Phe Val Trp Ala Val Leu Ile Ala Asn Leu Ala
        115                 120                 125

His Ile Gly Tyr Glu Glu Lys Asn Met Tyr Met Ala Ala Tyr Asp Trp
    130                 135                 140

Arg Leu Ser Phe Gln Asn Thr Glu Val Arg Asp Gln Thr Leu Ser Arg
145                 150                 155                 160

Met Lys Ser Asn Ile Glu Leu Met Val Ser Thr Asn Gly Gly Lys Lys
                165                 170                 175

Ala Val Ile Val Pro His Ser Met Gly Val Leu Tyr Phe Leu His Phe
            180                 185                 190

Met Lys Trp Val Glu Ala Pro Ala Pro Leu Gly Gly Gly Gly Gly Pro
        195                 200                 205

Asp Trp Cys Ala Lys Tyr Ile Lys Ala Val Met Asn Ile Gly Gly Pro
    210                 215                 220

Phe Leu Gly Val Pro Lys Ala Val Ala Gly Leu Phe Ser Ala Glu Ala
225                 230                 235                 240

Lys Asp Val Ala Val Ala Arg Ala Ile Ala Pro Gly Phe Leu Asp Thr
                245                 250                 255

Asp Ile Phe Arg Leu Gln Thr Leu Gln His Val Met Arg Met Thr Arg
            260                 265                 270

Thr Trp Asp Ser Thr Met Ser Met Leu Pro Lys Gly Gly Asp Thr Ile
        275                 280                 285

Trp Gly Gly Leu Asp Trp Ser Pro Glu Lys Gly His Thr Cys Cys Gly
    290                 295                 300

Lys Lys Gln Lys Asn Asn Glu Thr Cys Gly Glu Ala Gly Glu Asn Gly
305                 310                 315                 320

Val Ser Lys Lys Ser Pro Val Asn Tyr Gly Arg Met Ile Ser Phe Gly
                325                 330                 335

Lys Glu Val Ala Glu Ala Ala Pro Ser Glu Ile Asn Asn Ile Asp Phe
```

-continued

```
            340                 345                 350

Arg Gly Ala Val Lys Gly Gln Ser Ile Pro Asn His Thr Cys Arg Asp
        355                 360                 365

Val Trp Thr Glu Tyr His Asp Met Gly Ile Ala Gly Ile Lys Ala Ile
    370                 375                 380

Ala Glu Tyr Lys Val Tyr Thr Ala Gly Glu Ala Ile Asp Leu Leu His
385                 390                 395                 400

Tyr Val Ala Pro Lys Met Met Ala Arg Gly Ala Ala His Phe Ser Tyr
                405                 410                 415

Gly Ile Ala Asp Asp Leu Asp Asp Thr Lys Tyr Gln Asp Pro Lys Tyr
            420                 425                 430

Trp Ser Asn Pro Leu Glu Thr Lys Leu Pro Asn Ala Pro Glu Met Glu
        435                 440                 445

Ile Tyr Ser Leu Tyr Gly Val Gly Ile Pro Thr Glu Arg Ala Tyr Val
    450                 455                 460

Tyr Lys Leu Asn Gln Ser Pro Asp Ser Cys Ile Pro Phe Gln Ile Phe
465                 470                 475                 480

Thr Ser Ala His Glu Glu Asp Glu Asp Ser Cys Leu Lys Ala Gly Val
                485                 490                 495

Tyr Asn Val Asp Gly Asp Glu Thr Val Pro Val Leu Ser Ala Gly Tyr
            500                 505                 510

Met Cys Ala Lys Ala Trp Arg Gly Lys Thr Arg Phe Asn Pro Ser Gly
        515                 520                 525

Ile Lys Thr Tyr Ile Arg Glu Tyr Asn His Ser Pro Pro Ala Asn Leu
    530                 535                 540

Leu Glu Gly Arg Gly Thr Gln Ser Gly Ala His Val Asp Ile Met Gly
545                 550                 555                 560

Asn Phe Ala Leu Ile Glu Asp Ile Met Arg Val Ala Ala Gly Gly Asn
                565                 570                 575

Gly Ser Asp Ile Gly His Asp Gln Val His Ser Gly Ile Phe Glu Trp
            580                 585                 590

Ser Glu Arg Ile Asp Leu Lys Leu
        595                 600
```

<210> SEQ ID NO 8
<211> LENGTH: 1902
<212> TYPE: DNA
<213> ORGANISM: Arabidopsis thaliana

<400> SEQUENCE: 8

```
atgggagcga attcgaaatc agtaacggct tccttcaccg tcatcgccgt tttttcttg      60

atttgcggtg gccgaacggc ggtggaggat gagaccgagt ttcacggcga ctactcgaag    120

ctatcgggta taatcattcc gggatttgcg tcgacgcagc tacgagcgtg gtcgatcctt    180

gactgtccat acactccgtt ggacttcaat ccgctcgacc tcgtatggct agacaccact    240

aagcttcttt ctgctgtcaa ctgctggttt aagtgtatgg tgctagatcc ttataatcaa    300

acagaccatc ccgagtgtaa gtcacggcct gacagtggtc tttcagccat cacagaattg    360

gatccaggtt acataacagg tcctctttct actgtctgga aagagtggct taagtggtgt    420

gttgagtttg gtgtagaagc aaatgcaatt gtcgctgttc catacgattg gagattgtca    480

ccaaccaaat tggaagagcg tgacctttac tttcacaagc tcaagttgac ctttgaaact    540

gctttaaaac tccgtggcgg cccttctata gtatttgccc attcaatggg taataatgtc    600

ttcagatact ttctggaatg gctgaggcta gaaattgcac caaaacatta tttgaagtgg    660
```

-continued

```
cttgatcagc atatccatgc ttatttcgct gttggagctc ctcttcttgg ttctgttgag    720

gcaatcaaat ctactctctc tggtgtaacg tttggccttc ctgtttctga gggaactgct    780

cggttgttgt ccaattcttt tgcgtcgtca ttgtggctta tgccattttc aaagaattgc    840

aagggtgata acacattctg gacgcatttt tctgggggtg ctgcaaagaa agataagcgc    900

gtataccact gtgatgaaga ggaatatcaa tcaaaatatt ctggctggcc gacaaatatt    960

attaacattg aaattccttc cactagcgtt acagaaacag ctctagtcaa catgaccagc   1020

atggaatgtg gcctccccac ccttttgtct ttcacagccc gtgaactagc agatgggact   1080

cttttcaaag caatagaaga ctatgaccca gatagcaaga ggatgttaca ccagttaaag   1140

aagttgtatc atgatgaccc tgtttttaat cctctgactc cttgggagag accacctata   1200

aaaaatgtat tttgcatata tggtgctcat ctaaagacag aggttggtta ttactttgcc   1260

ccaagtggca aaccttatcc tgataattgg atcatcacgg atatcattta tgaaactgaa   1320

ggttccctcg tgtcaaggtc tggaactgtg gttgatggga acgctggacc tataactggg   1380

gatgagacgg taccctatca ttcactctct tggtgcaaga attggctcgg acctaaagtt   1440

aacataacaa tggctcccca gccagaacac gatggaagcg acgtacatgt ggaactaaat   1500

gttgatcatg agcatgggtc agacatcata gctaacatga caaaagcacc aagggttaag   1560

tacataacct tttatgaaga ctctgagagc attccgggga agagaaccgc agtctgggag   1620

cttgataaaa caaatcacag gaacatagta agatctccag ttctgatgag ggagttatgg   1680

cttcagatgt ggcatgacat tcagcctggt gcaaagtcca aatttgtcac caaagccaag   1740

cgcgggccac ttagagatgc ggattgctac tgggattacg ggaaagcctg ttgtgcttgg   1800

caagaatact gtgaatacag atacagtttt ggggatgttc acttaggaca aagttgtaga   1860

ttgagaaaca catctgctaa tatgcttctc cagtacatat aa                      1902
```

```
<210> SEQ ID NO 9
<211> LENGTH: 633
<212> TYPE: PRT
<213> ORGANISM: Arabidopsis thaliana

<400> SEQUENCE: 9

Met Gly Ala Asn Ser Lys Ser Val Thr Ala Ser Phe Thr Val Ile Ala
1               5                   10                  15

Val Phe Phe Leu Ile Cys Gly Gly Arg Thr Ala Val Glu Asp Glu Thr
            20                  25                  30

Glu Phe His Gly Asp Tyr Ser Lys Leu Ser Gly Ile Ile Ile Pro Gly
        35                  40                  45

Phe Ala Ser Thr Gln Leu Arg Ala Trp Ser Ile Leu Asp Cys Pro Tyr
    50                  55                  60

Thr Pro Leu Asp Phe Asn Pro Leu Asp Leu Val Trp Leu Asp Thr Thr
65                  70                  75                  80

Lys Leu Leu Ser Ala Val Asn Cys Trp Phe Lys Cys Met Val Leu Asp
                85                  90                  95

Pro Tyr Asn Gln Thr Asp His Pro Glu Cys Lys Ser Arg Pro Asp Ser
            100                 105                 110

Gly Leu Ser Ala Ile Thr Glu Leu Asp Pro Gly Tyr Ile Thr Gly Pro
        115                 120                 125

Leu Ser Thr Val Trp Lys Glu Trp Leu Lys Trp Cys Val Glu Phe Gly
    130                 135                 140

Val Glu Ala Asn Ala Ile Val Ala Val Pro Tyr Asp Trp Arg Leu Ser
```

-continued 145 150 155 160

Pro Thr Lys Leu Glu Glu Arg Asp Leu Tyr Phe His Lys Leu Lys Leu
165 170 175

Thr Phe Glu Thr Ala Leu Lys Leu Arg Gly Gly Pro Ser Ile Val Phe
180 185 190

Ala His Ser Met Gly Asn Asn Val Phe Arg Tyr Phe Leu Glu Trp Leu
195 200 205

Arg Leu Glu Ile Ala Pro Lys His Tyr Leu Lys Trp Leu Asp Gln His
210 215 220

Ile His Ala Tyr Phe Ala Val Gly Ala Pro Leu Leu Gly Ser Val Glu
225 230 235 240

Ala Ile Lys Ser Thr Leu Ser Gly Val Thr Phe Gly Leu Pro Val Ser
245 250 255

Glu Gly Thr Ala Arg Leu Leu Ser Asn Ser Phe Ala Ser Ser Leu Trp
260 265 270

Leu Met Pro Phe Ser Lys Asn Cys Lys Gly Asp Asn Thr Phe Trp Thr
275 280 285

His Phe Ser Gly Gly Ala Ala Lys Lys Asp Lys Arg Val Tyr His Cys
290 295 300

Asp Glu Glu Glu Tyr Gln Ser Lys Tyr Ser Gly Trp Pro Thr Asn Ile
305 310 315 320

Ile Asn Ile Glu Ile Pro Ser Thr Ser Val Thr Glu Thr Ala Leu Val
325 330 335

Asn Met Thr Ser Met Glu Cys Gly Leu Pro Thr Leu Leu Ser Phe Thr
340 345 350

Ala Arg Glu Leu Ala Asp Gly Thr Leu Phe Lys Ala Ile Glu Asp Tyr
355 360 365

Asp Pro Asp Ser Lys Arg Met Leu His Gln Leu Lys Lys Leu Tyr His
370 375 380

Asp Asp Pro Val Phe Asn Pro Leu Thr Pro Trp Glu Arg Pro Pro Ile
385 390 395 400

Lys Asn Val Phe Cys Ile Tyr Gly Ala His Leu Lys Thr Glu Val Gly
405 410 415

Tyr Tyr Phe Ala Pro Ser Gly Lys Pro Tyr Pro Asp Asn Trp Ile Ile
420 425 430

Thr Asp Ile Ile Tyr Glu Thr Glu Gly Ser Leu Val Ser Arg Ser Gly
435 440 445

Thr Val Val Asp Gly Asn Ala Gly Pro Ile Thr Gly Asp Glu Thr Val
450 455 460

Pro Tyr His Ser Leu Ser Trp Cys Lys Asn Trp Leu Gly Pro Lys Val
465 470 475 480

Asn Ile Thr Met Ala Pro Gln Pro Glu His Asp Gly Ser Asp Val His
485 490 495

Val Glu Leu Asn Val Asp His Glu His Gly Ser Asp Ile Ile Ala Asn
500 505 510

Met Thr Lys Ala Pro Arg Val Lys Tyr Ile Thr Phe Tyr Glu Asp Ser
515 520 525

Glu Ser Ile Pro Gly Lys Arg Thr Ala Val Trp Glu Leu Asp Lys Thr
530 535 540

Asn His Arg Asn Ile Val Arg Ser Pro Val Leu Met Arg Glu Leu Trp
545 550 555 560

Leu Gln Met Trp His Asp Ile Gln Pro Gly Ala Lys Ser Lys Phe Val
565 570 575

-continued

```
Thr Lys Ala Lys Arg Gly Pro Leu Arg Asp Ala Asp Cys Tyr Trp Asp
            580                 585                 590

Tyr Gly Lys Ala Cys Cys Ala Trp Gln Glu Tyr Cys Glu Tyr Arg Tyr
        595                 600                 605

Ser Phe Gly Asp Val His Leu Gly Gln Ser Cys Arg Leu Arg Asn Thr
    610                 615                 620

Ser Ala Asn Met Leu Leu Gln Tyr Ile
625                 630


<210> SEQ ID NO 10
<211> LENGTH: 1299
<212> TYPE: DNA
<213> ORGANISM: Arabidopsis thaliana

<400> SEQUENCE: 10

atgaaaaaaa tatcttcaca ttattcggta gtcatagcga tactcgttgt ggtgacgatg      60

acctcgatgt gtcaagccgt gggtagcaat gtgtaccctt tgattctggt tccaggaaac     120

ggaggtaacc agctagaggt acggctggac agagaataca agccaagtag tgtctggtgt     180

agcagctggt tatatccgat tcataagaag agtggtggat ggtttaggct atggttcgat     240

gcagcagtgt tattgtctcc cttcaccagg tgcttcagcg atcgaatgat gttgtactat     300

gaccctgatt tggatgatta ccaaaatgct cctggtgtcc aaacccgggt tcctcatttc     360

ggttcgacca aatcacttct atacctcgac cctcgtctcc gagatgccac atcttacatg     420

gaacatttgg cgaaagctct agagaaaaaa tgcgggtatg ttaacgacca aaccatccta     480

ggagctccat atgatttcag gtacggcctg gctgcttcgg gccacccgtc ccgtgtagcc     540

tcacagttcc tacaagacct caaacaattg gtggaaaaaa ctagcagcga gaacgaagga     600

aagccagtga tactcctctc ccatagccta ggaggacttt tcgtcctcca tttcctcaac     660

cgtaccaccc cttcatggcg ccgcaagtac atcaaacact ttgttgcact cgctgcgcca     720

tggggtggga cgatctctca gatgaagaca tttgcttctg gcaacacact cggtgtccct     780

ttagttaacc ctttgctggt cagacggcat cagaggacct ccgagagtaa ccaatggcta     840

cttccatcta ccaaagtgtt tcacgacaga actaaaccgc ttgtcgtaac tccccaggtt     900

aactacacag cttacgagat ggatcggttt tttgcagaca ttggattctc acaaggagtt     960

gtgccttaca agacaagagt gttgccttta acagaggagc tgatgactcc gggagtgcca    1020

gtcacttgca tatatgggag aggagttgat acaccggagg ttttgatgta tggaaaagga    1080

ggattcgata agcaaccaga gattaagtat ggagatggag atgggacggt taatttggcg    1140

agcctagcag ctttgaaagt cgatggcttg aacaccgtag agattgatgg agtttcgcat    1200

acatctatac ttaaagacga gatcgcactt aaagagatta tgaagcagat ttcaattatt    1260

aattatgaat tagcctatgt taatgccgtc aatgaatga                           1299


<210> SEQ ID NO 11
<211> LENGTH: 432
<212> TYPE: PRT
<213> ORGANISM: Arabidopsis thaliana

<400> SEQUENCE: 11

Met Lys Lys Ile Ser Ser His Tyr Ser Val Val Ile Ala Ile Leu Val
1               5                   10                  15

Val Val Thr Met Thr Ser Met Cys Gln Ala Val Gly Ser Asn Val Tyr
            20                  25                  30
```

-continued

```
Pro Leu Ile Leu Val Pro Gly Asn Gly Gly Asn Gln Leu Glu Val Arg
        35                  40                  45

Leu Asp Arg Glu Tyr Lys Pro Ser Ser Val Trp Cys Ser Ser Trp Leu
    50                  55                  60

Tyr Pro Ile His Lys Lys Ser Gly Gly Trp Phe Arg Leu Trp Phe Asp
65                  70                  75                  80

Ala Ala Val Leu Leu Ser Pro Phe Thr Arg Cys Phe Ser Asp Arg Met
                85                  90                  95

Met Leu Tyr Tyr Asp Pro Asp Leu Asp Asp Tyr Gln Asn Ala Pro Gly
            100                 105                 110

Val Gln Thr Arg Val Pro His Phe Gly Ser Thr Lys Ser Leu Leu Tyr
        115                 120                 125

Leu Asp Pro Arg Leu Arg Asp Ala Thr Ser Tyr Met Glu His Leu Val
    130                 135                 140

Lys Ala Leu Glu Lys Lys Cys Gly Tyr Val Asn Asp Gln Thr Ile Leu
145                 150                 155                 160

Gly Ala Pro Tyr Asp Phe Arg Tyr Gly Leu Ala Ala Ser Gly His Pro
                165                 170                 175

Ser Arg Val Ala Ser Gln Phe Leu Gln Asp Leu Lys Gln Leu Val Glu
            180                 185                 190

Lys Thr Ser Ser Glu Asn Glu Gly Lys Pro Val Ile Leu Leu Ser His
        195                 200                 205

Ser Leu Gly Gly Leu Phe Val Leu His Phe Leu Asn Arg Thr Thr Pro
    210                 215                 220

Ser Trp Arg Arg Lys Tyr Ile Lys His Phe Val Ala Leu Ala Ala Pro
225                 230                 235                 240

Trp Gly Gly Thr Ile Ser Gln Met Lys Thr Phe Ala Ser Gly Asn Thr
                245                 250                 255

Leu Gly Val Pro Leu Val Asn Pro Leu Leu Val Arg Arg His Gln Arg
            260                 265                 270

Thr Ser Glu Ser Asn Gln Trp Leu Leu Pro Ser Thr Lys Val Phe His
        275                 280                 285

Asp Arg Thr Lys Pro Leu Val Val Thr Pro Gln Val Asn Tyr Thr Ala
    290                 295                 300

Tyr Glu Met Asp Arg Phe Phe Ala Asp Ile Gly Phe Ser Gln Gly Val
305                 310                 315                 320

Val Pro Tyr Lys Thr Arg Val Leu Pro Leu Thr Glu Glu Leu Met Thr
                325                 330                 335

Pro Gly Val Pro Val Thr Cys Ile Tyr Gly Arg Gly Val Asp Thr Pro
            340                 345                 350

Glu Val Leu Met Tyr Gly Lys Gly Gly Phe Asp Lys Gln Pro Glu Ile
        355                 360                 365

Lys Tyr Gly Asp Gly Asp Gly Thr Val Asn Leu Ala Ser Leu Ala Ala
    370                 375                 380

Leu Lys Val Asp Ser Leu Asn Thr Val Glu Ile Asp Gly Val Ser His
385                 390                 395                 400

Thr Ser Ile Leu Lys Asp Glu Ile Ala Leu Lys Glu Ile Met Lys Gln
                405                 410                 415

Ile Ser Ile Ile Asn Tyr Glu Leu Ala Asn Val Asn Ala Val Asn Glu
            420                 425                 430
```

<210> SEQ ID NO 12
<211> LENGTH: 1998
<212> TYPE: DNA

-continued

<213> ORGANISM: Arabidopsis thaliana

<400> SEQUENCE: 12
atgtctccac ttctccggtt tagaaaacta tcgtccttct ctgaagatac cattaaccct 60
aaacccaaac aatcggcaac cgtcgagaaa ccaaaacggc gccgttccgg gagatgtagc 120
tgcgttgact catgttgctg gttgattggt tatctctgta cggcgtggtg gcttctcctc 180
tttctttacc actctgttcc ggtcccggcg atgcttcaag ctccggagtc tccgggaact 240
cggttgagtc gagacggtgt caaggcgttt catccggtga ttcttgttcc ggggattgta 300
accggcgggc tcgagctttg ggaaggtcgg ccttgcgctg aaggactctt tcgtaaacgt 360
ctttggggtg ctagcttctc cgagattctt agaaggccat tgtgctggtt ggagcactta 420
tctctagaca gtgagaccgg tctcgatcca tcgggaatcc gtgtccgagc agtcccagga 480
ctagtggctg cagactattt cgcaccatgc tactttgctt gggcagttct catagagaat 540
ttggcaaaaa ttggatatga aggcaagaac cttcacatgg cctcttatga ttggagactc 600
tctttccata acaccgaggt acgtgaccaa tcgttaagta gactgaagag caaaatcgag 660
ctaatgtatg ccaccaatgg gtttaagaaa gttgtggtgg ttccgcattc aatgggggct 720
atctatttcc ttcacttcct taaatgggta gaaacacctc ttcctgatgg aggcggtggg 780
ggtggtccag gttggtgtgc caaacacatc aaatccgtcg tcaacattgg acccgccttt 840
ttaggtgttc ctaaagccgt cagtaattta ctttctgctg aaggcaaaga catcgcttac 900
gccagatctt tggctccagg tctcttggac tcggaacttc tcaagctgca aacactcgaa 960
caccttatgc ggatgtcaca tagctgggat tcaatagtat ctttattacc aaagggcggt 1020
gaggcaattt ggggcgatct agactcgcac gctgaagaag gactcaattg tatttactcc 1080
aagagaaaat catcgcagct atcgctaagt aatctccata aacaaaacta cagccttaaa 1140
ccggtgtcac gggtgaaaga acccgcaaag tacggaagaa tcgtatcttt cgggaaacga 1200
gcatcagaac tgccttcctc acaactctct acgctaaacg tcaaggaact gtcaagagta 1260
gatggcaatt caaatgacag tacatcatgt ggagagtttt ggtcagagta caatgaaatg 1320
agccgagaaa gcatagtaaa agtagcagaa aacacagctt atacagccac cactgttctt 1380
gatcttcttc gatttatagc ccctaagatg atgagacgag ccgaagctca tttctctcac 1440
ggcattgctg atgatcttga tgaccctaag tatggacatt ataagtactg gtctaatcca 1500
ctcgagacca aattaccgga ggcaccagag atggaaatgt actgtcttta cggagtaggg 1560
attccgaccg agagatctta catatacaag ctcgcaacct cttccggtaa atgcaagagc 1620
agcattccct tccggataga tggatctctg gatggagatg acgtttgtct taagggagga 1680
acacggtttg cggacggaga cgagagtgta ccggtgataa gtgcggggtt tatgtgcgca 1740
aagggatgga gaggaaaaac acggtttaac ccgtcaggga tggatacatt cttgcgggaa 1800
tacaaacata agccgccggg aagtctacta gaaagtcgag gaacggaaag cggagctcat 1860
gtagacataa tgggtaatgt tggactcatt gaagatgttt tgaggatagc tgccggagct 1920
tcaggccagg agattggtgg cgatagaatt tactcggatg tgatgaggat gtcggagaga 1980
attagcatca agttgtga 1998

<210> SEQ ID NO 13
<211> LENGTH: 665
<212> TYPE: PRT
<213> ORGANISM: Arabidopsis thaliana

<400> SEQUENCE: 13

-continued

```
Met Ser Pro Leu Leu Arg Phe Arg Lys Leu Ser Ser Phe Ser Glu Asp
1               5                   10                  15

Thr Ile Asn Pro Lys Pro Lys Gln Ser Ala Thr Val Glu Lys Pro Lys
            20                  25                  30

Arg Arg Arg Ser Gly Arg Cys Ser Cys Val Asp Ser Cys Cys Trp Leu
        35                  40                  45

Ile Gly Tyr Leu Cys Thr Ala Trp Trp Leu Leu Leu Phe Leu Tyr His
    50                  55                  60

Ser Val Pro Val Pro Ala Met Leu Gln Ala Pro Glu Ser Pro Gly Thr
65                  70                  75                  80

Arg Leu Ser Arg Asp Gly Val Lys Ala Phe His Pro Val Ile Leu Val
                85                  90                  95

Pro Gly Ile Val Thr Gly Gly Leu Glu Leu Trp Glu Gly Arg Pro Cys
            100                 105                 110

Ala Glu Gly Leu Phe Arg Lys Arg Leu Trp Gly Ala Ser Phe Ser Glu
        115                 120                 125

Ile Leu Arg Arg Pro Leu Cys Trp Leu Glu His Leu Ser Leu Asp Ser
    130                 135                 140

Glu Thr Gly Leu Asp Pro Ser Gly Ile Arg Val Arg Ala Val Pro Gly
145                 150                 155                 160

Leu Val Ala Ala Asp Tyr Phe Ala Pro Cys Tyr Phe Ala Trp Ala Val
                165                 170                 175

Leu Ile Glu Asn Leu Ala Lys Ile Gly Tyr Glu Gly Lys Asn Leu His
            180                 185                 190

Met Ala Ser Tyr Asp Trp Arg Leu Ser Phe His Asn Thr Glu Val Arg
        195                 200                 205

Asp Gln Ser Leu Ser Arg Leu Lys Ser Lys Ile Glu Leu Met Tyr Ala
    210                 215                 220

Thr Asn Gly Phe Lys Lys Val Val Val Val Pro His Ser Met Gly Ala
225                 230                 235                 240

Ile Tyr Phe Leu His Phe Leu Lys Trp Val Glu Thr Pro Leu Pro Asp
                245                 250                 255

Gly Gly Gly Gly Gly Gly Pro Gly Trp Cys Ala Lys His Ile Lys Ser
            260                 265                 270

Val Val Asn Ile Gly Pro Ala Phe Leu Gly Val Pro Lys Ala Val Ser
        275                 280                 285

Asn Leu Leu Ser Ala Glu Gly Lys Asp Ile Ala Tyr Ala Arg Ser Leu
    290                 295                 300

Ala Pro Gly Leu Leu Asp Ser Glu Leu Leu Lys Leu Gln Thr Leu Glu
305                 310                 315                 320

His Leu Met Arg Met Ser His Ser Trp Asp Ser Ile Val Ser Leu Leu
                325                 330                 335

Pro Lys Gly Gly Glu Ala Ile Trp Gly Asp Leu Asp Ser His Ala Glu
            340                 345                 350

Glu Gly Leu Asn Cys Ile Tyr Ser Lys Arg Lys Ser Ser Gln Leu Ser
        355                 360                 365

Leu Ser Asn Leu His Lys Gln Asn Tyr Ser Leu Lys Pro Val Ser Arg
    370                 375                 380

Val Lys Glu Pro Ala Lys Tyr Gly Arg Ile Val Ser Phe Gly Lys Arg
385                 390                 395                 400

Ala Ser Glu Leu Pro Ser Ser Gln Leu Ser Thr Leu Asn Val Lys Glu
                405                 410                 415
```

-continued

```
Leu Ser Arg Val Asp Gly Asn Ser Asn Asp Ser Thr Ser Cys Gly Glu
            420                 425                 430

Phe Trp Ser Glu Tyr Asn Glu Met Ser Arg Glu Ser Ile Val Lys Val
        435                 440                 445

Ala Glu Asn Thr Ala Tyr Thr Ala Thr Thr Val Leu Asp Leu Leu Arg
    450                 455                 460

Phe Ile Ala Pro Lys Met Met Arg Arg Ala Glu Ala His Phe Ser His
465                 470                 475                 480

Gly Ile Ala Asp Asp Leu Asp Asp Pro Lys Tyr Gly His Tyr Lys Tyr
                485                 490                 495

Trp Ser Asn Pro Leu Glu Thr Lys Leu Pro Glu Ala Pro Glu Met Glu
            500                 505                 510

Met Tyr Cys Leu Tyr Gly Val Gly Ile Pro Thr Glu Arg Ser Tyr Ile
        515                 520                 525

Tyr Lys Leu Ala Thr Ser Ser Gly Lys Cys Lys Ser Ser Ile Pro Phe
    530                 535                 540

Arg Ile Asp Gly Ser Leu Asp Gly Asp Asp Val Cys Leu Lys Gly Gly
545                 550                 555                 560

Thr Arg Phe Ala Asp Gly Asp Glu Ser Val Pro Val Ile Ser Ala Gly
                565                 570                 575

Phe Met Cys Ala Lys Gly Trp Arg Gly Lys Thr Arg Phe Asn Pro Ser
            580                 585                 590

Gly Met Asp Thr Phe Leu Arg Glu Tyr Lys His Lys Pro Pro Gly Ser
        595                 600                 605

Leu Leu Glu Ser Arg Gly Thr Glu Ser Gly Ala His Val Asp Ile Met
    610                 615                 620

Gly Asn Val Gly Leu Ile Glu Asp Val Leu Arg Ile Ala Ala Gly Ala
625                 630                 635                 640

Ser Gly Gln Glu Ile Gly Gly Asp Arg Ile Tyr Ser Asp Val Met Arg
                645                 650                 655

Met Ser Glu Arg Ile Ser Ile Lys Leu
            660                 665
```

<210> SEQ ID NO 14
<211> LENGTH: 2047
<212> TYPE: DNA
<213> ORGANISM: Aspergillus nidulans

<400> SEQUENCE: 14

```
cttcggtatt attgtatgag ggtgtttttt tgaagtcggc gtctgaacgt caaaaagtac     60

ggcgcatgtg attgcgagct tatcgggtcg atggccttga ttccatcgat ctattaccca    120

caaactccca tcttctctat tattctctat tctacggtgt acaattactt cttcgtgata    180

tcgcttcgcc ttttacctct ctccttttct catttaccgc gttcccatac cctaccgcag    240

ccgatccgct ggcgatcgct gcccgtctcc atctatgatt cgtcgtcgcc aggccaaaga    300

caacagcgac gatgtccagg cgccagctcc cacggactcg tcaccagaaa aacagctccc    360

accggcagtg gcgaagccta agaatgagag gaagcaatca tttatcacga aacccaagag    420

caagcggcgc aatggactca tcttcctgct gggcggagtc ttcgggatct tctgcgcggt    480

tttcttcgct cagcagcagg acgtcattag cctggactct ttaatggatg tgaatataga    540

ctcgttaatg gatgtcattc ctcaaagtat aatgcgggat gcgcgggagt tttcggtatg    600

ttactgtctt gagatctgat ggagtggtgc taatagtggt tgactgcagc aacatgaacg    660

cgatactgtc agttatgatg ctttctctgt cggcctacat cttcggtctc agggggttga    720
```

-continued

```
agcgaaacac ccgattatca tgatccctgg tgttatatcg acgggactcg agagctgggg    780

aactagtcct acgtcactga tgtactttcg gcgcagactc tggggcagtt ggagtatgat    840

gcgggcacta gtgctggaca agacggagtg gaagaatcat atcatgctgg ataaagagac    900

tgggctggac ccgccgggga ttaagctgcg tgcggcccag gggttcgatg ccacggactt    960

tttcatcaca gggtactgga tctggaataa gatcctagag aaccttgcga gtattggtta   1020

tgacccgaca aacgcctaca cagcggctta tgactggcga ttatcttatt tgaggggga    1080

ggttttggac cactacttta gccggctgaa gtcgtacatt gagaccgcgg tgcaggtgcg   1140

tggtgagaag gtgacgcttg cctcgcacag tatggggtca caagtggtcc tcttcttctt   1200

taaatgggta gagaacccag cacacgggaa gggcggctcc gactgggtta atcgacacat   1260

cgccaactgg atcaacatca gcgggtgcat gctaggcgcc gcccaaggcc tcacagccgt   1320

gctgtccggc gagacacgag atacagcgct gctcaaactt cgttcgccgt ctacgggctg   1380

gagaagttcc tctcccgcga agaacgcgcc gagattttcc gcgcaatgcc cggcatctcc   1440

agcatgctcc ccaagggcgg cgaagcagtc tggggcaatt ccacctgggc tccggacgac   1500

caaccaggcc agaagattac ctatggcaac atccttaact tccgcgaaac aaactccacc   1560

ttcacgcaga aaaacctcac cgttcccgaa agcctcgact acctcctcga ccagagcgag   1620

ccgtggtacc gcgaccaagt tttaggaagc tactcgcacg gcgtcgcaca cacaaccgcc   1680

gaagttgagg ccaacgagaa tgacccacgc acctggctga accctctcga ggctcgcctg   1740

ccacttgcac cagacatgaa actctattgc ttctacggcg tcggcaaacc gaccgagcga   1800

agctacttct atcaggagga acgggacccc ctcgttaatc ttaatgttag catcgataca   1860

accgtcacaa cggctgatgg aacggatcac ggcgtcgtcc ttggtgaggg cgacggcacc   1920

gtcaacctcc tgagcacggg ctatatgtgc gccaaaggtt ggcacatcaa gcggtataac   1980

ccatccggaa tcaagatcaa agtttacgaa atgccgcatg aaccggatcg gttttcgcct   2040

cgagtgg                                                             2047
```

<210> SEQ ID NO 15
<211> LENGTH: 2223
<212> TYPE: DNA
<213> ORGANISM: Aspergillus fumigatus

<400> SEQUENCE: 15

```
gtaaaaggac gaatgtgagc agcttgtgat tgcgctgtgt ctgatgatgg tggttggtgg     60

tccgagaaga caggaatttt gaggatctcg catgacgttc gggttcctgt ttcccatgtg    120

atttcgacga ccgtcgctgt tcttgggtac cttttttat tgtttattct agcttctcac     180

tttcaattct ttttatctac tttcctgtcg tccgattctc tgggccttag gagttattgt    240

cttcgagcta cactcccagt ctgagtttgg cgttacatca attgcagcat tttgctttcc    300

tttacgaccc ttcctggcgg tcgcccacat gctccgccgt cgtctggcaa aggacgacga    360

cgtccagcag actaaggaca agtctcgcga tgacaaagga aagtcatcgc cagatactaa    420

gacggttgtt atccaagaaa agccgcaatc tggatcgttc ttttcccgac cgaagagtaa    480

acggcgcaat ggactcatct tcgcactagg aggcattttc ggcatctttg ttgccttgtt    540

tttcgccaac cagcaggatg tgattagtct tgaatcattg atggatctga acctggacac    600

attgatcgat gttattcctc aaggcattat aagggatgcg cgagagttca cggtatgttg    660

aaccattgat actcttgcca gttgttattc ctctatacta atcagcttcc cttgacatct    720
```

-continued

```
gtacagcaac atgagcgcga cgcagtcagc tatgatccct tctccgtcgg cctccagctt    780

caggcgcaag gcatcgaggc caaacatcca atcgttatga tccccggtgt catttcaacc    840

ggcttggaga gttggggcac agggccggcc tcccgtcagt actttcgtcg gcgactctgg    900

ggcagttgga gcatgatgcg tgcgctcgtt atggataaag cagaatggaa gaatcacatc    960

atgctggaca gagagactgg attagatcct ccggggatca agcttcgcgc agcccagggg   1020

ttcgatgcga ccgatttctt tatcacaggc tactggatct ggaacaagat ccttgagaat   1080

ctggccacga ttggatacga cccaaccaat gcttttacgg ccgcatatga ttggcggcta   1140

tcctatttaa acctggaagt ccgcgatcag tacttcagtc gtcttaagtc gtatatcgag   1200

acggctgtgc tggttaaagg agagaaggtg actctagcgt cgcacagtat gggttcgcag   1260

gtggttctct acttcttcaa atgggtcgaa catccagatc acggcaaagg aggtcgcgac   1320

tgggttaaca agcacatcgc caactggatc aacatcagcg ggtgcatgct aggcgccgtc   1380

aaaggcctga cggcggtgtt gtcgggcgag atgcgcgaca ccgcccaact taacgccttt   1440

gccgtctacg gcctggagaa gttcctgtcc aaggaagagc gtgccgagat cttccgcgcc   1500

atgccgggta tatcgagcat gctccccaag ggcggcgaag cagtctgggg caactctacc   1560

tgggcaccgg acgatcaacc tggccaagtc atgaccttcg gcaacctcct caacttccgc   1620

gaaaccaatt cctcctggac ccgtaaaaac ctcaccacaa cggaaagcct gacctacctg   1680

ctcgaccaaa gtgaggattg gtaccgccac caggtgctga gcagctattc acacggcgtc   1740

gcgcatacaa ccaaggaagt cgaggcgaac gagaacgacc cgcgcacatg gctcaaccca   1800

cttgagacac ggctgcccct cgccccggac atgaagatct actgcttcta cggtgtgggc   1860

aagccgacgg agcgcagtta cttttatcaa gaagaacgcg atcccctcgt caacctcaac   1920

gtcagcattg acaccaccgt gaccacgcca gacggcgtag atcgcggcgt tctcatgggt   1980

gagggcgatg gcacggttaa cctgctcagc acaggataca tgtgtggcca gggatggcat   2040

attaaacggg ataccccccc cgcgtgaaat caagtcttct agatgccgca tgagccaaac   2100

cgattctccc cccgcgtggg ccgaataaag ggaacttcat cttctgcctc attcaatcaa   2160

gtatttccgg ggggtactga ctgacgatca aactcaaagt ggatcaccgt ccaaacccta   2220

ggg                                                                 2223
```

<210> SEQ ID NO 16
<211> LENGTH: 1872
<212> TYPE: DNA
<213> ORGANISM: Schizosaccharomyces pombe

<400> SEQUENCE: 16

```
atggcgtctt ccaagaagag caaaactcat aagaaaaaga aagaagtcaa atctcctatc     60

gacttaccaa attcaaagaa accaactcgc gctttgagtg agcaaccttc agcgtccgaa    120

acacaatctg tttcaaataa atcaagaaaa tctaaatttg gaaaaagatt gaattttata    180

ttgggcgcta ttttgggaat atgcggtgct ttttttttcg ctgttggaga cgacaatgct    240

gttttcgacc ctgctacgtt agataaattt gggaatatgc taggctcttc agacttgttt    300

gatgacatta aaggatattt atcttataat gtgtttaagg atgcaccttt tactacggac    360

aagccttcgc agtctcctag cggaaatgaa gttcaagttg gtcttgatat gtacaatgag    420

ggatatcgaa gtgaccatcc tgttattatg gttcctggtg ttatcagctc aggattagaa    480

agttggtcgt ttaataattg ctcgattcct tactttagga aacgtctttg ggtagctgg    540

tctatgctga aggcaatgtt ccttgacaag caatgctggc ttgaacattt aatgcttgat    600
```

-continued

```
aaaaaaaccg gcttggatcc gaagggaatt aagctgcgag cagctcaggg gtttgaagca    660
gctgattttt ttatcacggg ctattggatt tggagtaaag taattgaaaa ccttgctgca    720
attggttatg agcctaataa catgttaagt gcttcttacg attggcggtt atcatatgca    780
aatttagagg aacgtgataa atatttttca aagttaaaaa tgttcattga gtacagcaac    840
attgtacata agaaaaaggt agtgttgatt tctcactcca tgggttcaca ggttacgtac    900
tatttttta agtgggttga agctgagggc tacggaaatg gtggaccgac ttgggttaat     960
gatcatattg aagcatttat aaatatatcg ggatctttga ttggagcacc caaaacagtg   1020
gcagcgcttt tatcgggtga aatgaaagat acaggtattg taattacatt aaacattttg   1080
gaaaaatttt tttcccgttc tgagagagcc atgatggttc gcactatggg aggagttagt   1140
tctatgcttc ctaaaggagg cgatgttgct ccagatgatc ttaatcaaac aaatttttcc   1200
aatggtgcaa ttattcgata tagagaagac attgataagg accacgatga atttgacata   1260
gatgatgcat tacaattttt aaaaaatgtt acagatgacg attttaaagt catgctagcg   1320
aaaaattatt cccacggtct tgcttggact gaaaaagaag tgttaaaaaa taacgaaatg   1380
ccgtctaaat ggataaatcc gctagaaact agtcttcctt atgctcctga tatgaaaatt   1440
tattgcgttc acggggtcgg aaaaccaact gagagaggtt attattatac taataatcct   1500
gaggggcaac ctgtcattga ttcctcggtt aatgatggaa caaaagttga aaatggtatt   1560
gttatggatg atggtgatgg aactttacca atattagccc ttggtttggt gtgcaataaa   1620
gtttggcaaa caaaaaggtt taatcctgct aatacaagta tcacaaatta tgaaatcaag   1680
catgaacctg ctgcgtttga tctgagagga ggacctcgct cggcagaaca cgtcgatata   1740
cttggacatt cagagctaaa tgaaattatt ttaaaagttt catcaggcca tggtgactcg   1800
gtaccaaacc gttatatatc agatatccag gaaataataa atgagataaa tctcgataaa   1860
cctagaaatt aa                                                       1872
```

<210> SEQ ID NO 17
<211> LENGTH: 623
<212> TYPE: PRT
<213> ORGANISM: Schizosaccharomyces pombe

<400> SEQUENCE: 17

```
Met Ala Ser Ser Lys Lys Ser Lys Thr His Lys Lys Lys Lys Glu Val
1               5                   10                  15

Lys Ser Pro Ile Asp Leu Pro Asn Ser Lys Lys Pro Thr Arg Ala Leu
            20                  25                  30

Ser Glu Gln Pro Ser Ala Ser Glu Thr Gln Ser Val Ser Asn Lys Ser
        35                  40                  45

Arg Lys Ser Lys Phe Gly Lys Arg Leu Asn Phe Ile Leu Gly Ala Ile
    50                  55                  60

Leu Gly Ile Cys Gly Ala Phe Phe Phe Ala Val Gly Asp Asp Asn Ala
65                  70                  75                  80

Val Phe Asp Pro Ala Thr Leu Asp Lys Phe Gly Asn Met Leu Gly Ser
                85                  90                  95

Ser Asp Leu Phe Asp Asp Ile Lys Gly Tyr Leu Ser Tyr Asn Val Phe
            100                 105                 110

Lys Asp Ala Pro Phe Thr Thr Asp Lys Pro Ser Gln Ser Pro Ser Gly
        115                 120                 125

Asn Glu Val Gln Val Gly Leu Asp Met Tyr Asn Glu Gly Tyr Arg Ser
    130                 135                 140
```

-continued

```
Asp His Pro Val Ile Met Val Pro Gly Val Ile Ser Ser Gly Leu Glu
145                 150                 155                 160

Ser Trp Ser Phe Asn Asn Cys Ser Ile Pro Tyr Phe Arg Lys Arg Leu
                165                 170                 175

Trp Gly Ser Trp Ser Met Leu Lys Ala Met Phe Leu Asp Lys Gln Cys
            180                 185                 190

Trp Leu Glu His Leu Met Leu Asp Lys Lys Thr Gly Leu Asp Pro Lys
        195                 200                 205

Gly Ile Lys Leu Arg Ala Ala Gln Gly Phe Glu Ala Ala Asp Phe Phe
    210                 215                 220

Ile Thr Gly Tyr Trp Ile Trp Ser Lys Val Ile Glu Asn Leu Ala Ala
225                 230                 235                 240

Ile Gly Tyr Glu Pro Asn Asn Met Leu Ser Ala Ser Tyr Asp Trp Arg
                245                 250                 255

Leu Ser Tyr Ala Asn Leu Glu Glu Arg Asp Lys Tyr Phe Ser Lys Leu
            260                 265                 270

Lys Met Phe Ile Glu Tyr Ser Asn Ile Val His Lys Lys Lys Val Val
        275                 280                 285

Leu Ile Ser His Ser Met Gly Ser Gln Val Thr Tyr Tyr Phe Phe Lys
    290                 295                 300

Trp Val Glu Ala Glu Gly Tyr Gly Asn Gly Gly Pro Thr Trp Val Asn
305                 310                 315                 320

Asp His Ile Glu Ala Phe Ile Asn Ile Ser Gly Ser Leu Ile Gly Ala
                325                 330                 335

Pro Lys Thr Val Ala Ala Leu Leu Ser Gly Glu Met Lys Asp Thr Gly
            340                 345                 350

Ile Val Ile Thr Leu Asn Ile Leu Glu Lys Phe Phe Ser Arg Ser Glu
        355                 360                 365

Arg Ala Met Met Val Arg Thr Met Gly Gly Val Ser Ser Met Leu Pro
    370                 375                 380

Lys Gly Gly Asp Val Ala Pro Asp Asp Leu Asn Gln Thr Asn Phe Ser
385                 390                 395                 400

Asn Gly Ala Ile Ile Arg Tyr Arg Glu Asp Ile Asp Lys Asp His Asp
                405                 410                 415

Glu Phe Asp Ile Asp Asp Ala Leu Gln Phe Leu Lys Asn Val Thr Asp
            420                 425                 430

Asp Asp Phe Lys Val Met Leu Ala Lys Asn Tyr Ser His Gly Leu Ala
        435                 440                 445

Trp Thr Glu Lys Glu Val Leu Lys Asn Asn Glu Met Pro Ser Lys Trp
    450                 455                 460

Ile Asn Pro Leu Glu Thr Ser Leu Pro Tyr Ala Pro Asp Met Lys Ile
465                 470                 475                 480

Tyr Cys Val His Gly Val Gly Lys Pro Thr Glu Arg Gly Tyr Tyr Tyr
                485                 490                 495

Thr Asn Asn Pro Glu Gly Gln Pro Val Ile Asp Ser Ser Val Asn Asp
            500                 505                 510

Gly Thr Lys Val Glu Asn Gly Ile Val Met Asp Asp Gly Asp Gly Thr
        515                 520                 525

Leu Pro Ile Leu Ala Leu Gly Leu Val Cys Asn Lys Val Trp Gln Thr
    530                 535                 540

Lys Arg Phe Asn Pro Ala Asn Thr Ser Ile Thr Asn Tyr Glu Ile Lys
545                 550                 555                 560
```

-continued

```
His Glu Pro Ala Ala Phe Asp Leu Arg Gly Gly Pro Arg Ser Ala Glu
                565                 570                 575

His Val Asp Ile Leu Gly His Ser Glu Leu Asn Glu Ile Ile Leu Lys
            580                 585                 590

Val Ser Ser Gly His Gly Asp Ser Val Pro Asn Arg Tyr Ile Ser Asp
        595                 600                 605

Ile Gln Glu Ile Ile Asn Glu Ile Asn Leu Asp Lys Pro Arg Asn
    610                 615                 620


<210> SEQ ID NO 18
<211> LENGTH: 2016
<212> TYPE: DNA
<213> ORGANISM: Crepis palaestina

<400> SEQUENCE: 18

atggcactaa ctcggagacg gaagcaacca gaggacgaaa cacagcagca tccggatccg      60

aaaccagacc aagaggatga taaggaagaa aaggcattaa agagatcagg aaaaaaggat     120

aagagcaaga actattcgtg tctggataac tgttgttggt tcgtaggatg cgtatgcacg     180

gcgtggtggc tactgttgtt tctatacaac gcgatgcctg cctctttccc gcaatttgtg     240

acggaggcaa tcactggacc gttgccggat cctccaggtg tcaaatgttt gaaagaaggt     300

ttgaaagtga agcatccggt ggtgtgtgtg ccggggattg tcaccggtgg acttgagctg     360

tgggaggggc atcagtgtat ggatggattg ttccgcaaga ggctttgggg tgggacgttt     420

ggcgaagtct ataagagacc ttcgtgctgg gtacagcata tgtcgctaga caacaaaaca     480

gggatggatc cgccagggat tcgggtcaga cccgtcagtg gacttgtagc tgctgactac     540

tttgctccgg gatattttgt atgggctgtt ttgatcgcta acttagctcg agttgggtat     600

gaagagaaga atatgtatat ggccgcatat gactggagac tctcatttca aaatacagag     660

gtaagagacc aatctttgag ccggataaag agcaatatag aacttatggt tgctacaaat     720

ggcggcaata aagcagttgt aattccacat tcaatgggtg ttatatactt tttgcatttc     780

atgaaatggg tggaagcacc ggctccaatg ggaggtggtg gtggaccaga ctggtgtgct     840

aaacacataa aggcagtcat gaatattggt ggtccctttt taggtgtccc aaaagcagta     900

gctgggcttt tttctgcaga agccaaggat attgcatcag ctagggcact tgcgccaaat     960

gtgctggact cggatttgtt tcagattcaa acgctgcaac atttaatgag aatgagtcgc    1020

acgtgggatt caactatgtc catgatacca aaaggtgggg acacgatttg ggtggcctt     1080

gattggtcac ctgaagaagg ttattgtcca agtaagagaa aggataggaa aaatgatacc    1140

gagaattcta ccgaaaaaga gtcaacaggt gaagaatgtg aagcaataca tgcgaattat    1200

ggaaggatgg tgtcatttgg agaagatgtt gcggatgcac catcatccga gattgaaagg    1260

gtagaattta ggggtgcggt gaaaggtcac aatgtggcaa acaatacatg ccgggacgtg    1320

tggactgaat accatgatat gggatttagt ggtattaagg ctgttgcaga atacaaagtg    1380

tatacggctg gagagattgt ggatatgctc gaatttgttg cccctaaaat gatggaaaga    1440

ggaagttttc atttttctta tggaatcgcg gaggatttag aggaccctaa atatgaacat    1500

tacaaatact ggtccaaccc cttggagtca aagttaccaa atgctcccga catggagatc    1560

tattccatgt acggagtcgg aatcccaacc gaaagagcat acgtgtacaa actcacacca    1620

gcagcagaat gctacattcc attccaaatt gacacgtcag caaaggataa aaacgaggac    1680

agctgtttaa aagatggtgt ttatacagtt tcaggggacg aaaccgtgcc agcattaagt    1740

gcaggatata tgtgtgcaaa aggttggcgt gggaaaaccc gattcaatcc ttccggaatc    1800
```

-continued aagacatatg ttagggtata tgatcacaat cctccagcta acttccttga gggtcggggg 1860
actttgagcg gggcccacgt tgacataatg gggaattttc agttgattga agatgttatt 1920
aaaattgcgg ctgggggcac gggtgaagaa gtgggaggcg atcaggtgta cgcgggaata 1980
tttgactggt ctgagaaaat taaattgaag ttatga 2016

<210> SEQ ID NO 19
<211> LENGTH: 671
<212> TYPE: PRT
<213> ORGANISM: Crepis palaestina

<400> SEQUENCE: 19

Met Ala Leu Thr Arg Arg Arg Lys Gln Pro Glu Asp Glu Thr Gln Gln
1 5 10 15

His Pro Asp Pro Lys Pro Asp Gln Glu Asp Asp Lys Glu Glu Lys Ala
20 25 30

Leu Lys Arg Ser Gly Lys Lys Asp Lys Ser Lys Asn Tyr Ser Cys Leu
35 40 45

Asp Asn Cys Cys Trp Phe Val Gly Cys Val Cys Thr Ala Trp Trp Leu
50 55 60

Leu Leu Phe Leu Tyr Asn Ala Met Pro Ala Ser Phe Pro Gln Phe Val
65 70 75 80

Thr Glu Ala Ile Thr Gly Pro Leu Pro Asp Pro Pro Gly Val Lys Cys
85 90 95

Leu Lys Glu Gly Leu Lys Val Lys His Pro Val Val Cys Val Pro Gly
100 105 110

Ile Val Thr Gly Gly Leu Glu Leu Trp Glu Gly His Gln Cys Met Asp
115 120 125

Gly Leu Phe Arg Lys Arg Leu Trp Gly Gly Thr Phe Gly Glu Val Tyr
130 135 140

Lys Arg Pro Ser Cys Trp Val Gln His Met Ser Leu Asp Asn Lys Thr
145 150 155 160

Gly Met Asp Pro Pro Gly Ile Arg Val Arg Pro Val Ser Gly Leu Val
165 170 175

Ala Ala Asp Tyr Phe Ala Pro Gly Tyr Phe Val Trp Ala Val Leu Ile
180 185 190

Ala Asn Leu Ala Arg Val Gly Tyr Glu Glu Lys Asn Met Tyr Met Ala
195 200 205

Ala Tyr Asp Trp Arg Leu Ser Phe Gln Asn Thr Glu Val Arg Asp Gln
210 215 220

Ser Leu Ser Arg Ile Lys Ser Asn Ile Glu Leu Met Val Ala Thr Asn
225 230 235 240

Gly Gly Asn Lys Ala Val Val Ile Pro His Ser Met Gly Val Ile Tyr
245 250 255

Phe Leu His Phe Met Lys Trp Val Glu Ala Pro Ala Pro Met Gly Gly
260 265 270

Gly Gly Gly Pro Asp Trp Cys Ala Lys His Ile Lys Ala Val Met Asn
275 280 285

Ile Gly Gly Pro Phe Leu Gly Val Pro Lys Ala Val Ala Gly Leu Phe
290 295 300

Ser Ala Glu Ala Lys Asp Ile Ala Ser Ala Arg Ala Leu Ala Pro Asn
305 310 315 320

Val Leu Asp Ser Asp Leu Phe Gln Ile Gln Thr Leu Gln His Leu Met
325 330 335

-continued

Arg Met Ser Arg Thr Trp Asp Ser Thr Met Ser Met Ile Pro Lys Gly
340 345 350

Gly Asp Thr Ile Trp Gly Gly Leu Asp Trp Ser Pro Glu Glu Gly Tyr
355 360 365

Cys Pro Ser Lys Arg Lys Asp Arg Lys Asn Asp Thr Glu Asn Ser Thr
370 375 380

Glu Lys Glu Ser Thr Gly Glu Glu Cys Glu Ala Ile His Ala Asn Tyr
385 390 395 400

Gly Arg Met Val Ser Phe Gly Glu Asp Val Ala Asp Ala Pro Ser Ser
405 410 415

Glu Ile Glu Arg Val Glu Phe Arg Gly Ala Val Lys Gly His Asn Val
420 425 430

Ala Asn Asn Thr Cys Arg Asp Val Trp Thr Glu Tyr His Asp Met Gly
435 440 445

Phe Ser Gly Ile Lys Ala Val Ala Glu Tyr Lys Val Tyr Thr Ala Gly
450 455 460

Glu Ile Val Asp Met Leu Glu Phe Val Ala Pro Lys Met Met Glu Arg
465 470 475 480

Gly Ser Phe His Phe Ser Tyr Gly Ile Ala Glu Asp Leu Glu Asp Pro
485 490 495

Lys Tyr Glu His Tyr Lys Tyr Trp Ser Asn Pro Leu Glu Ser Lys Leu
500 505 510

Pro Asn Ala Pro Asp Met Glu Ile Tyr Ser Met Tyr Gly Val Gly Ile
515 520 525

Pro Thr Glu Arg Ala Tyr Val Tyr Lys Leu Thr Pro Ala Ala Glu Cys
530 535 540

Tyr Ile Pro Phe Gln Ile Asp Thr Ser Ala Lys Asp Lys Asn Glu Asp
545 550 555 560

Ser Cys Leu Lys Asp Gly Val Tyr Thr Val Ser Gly Asp Glu Thr Val
565 570 575

Pro Ala Leu Ser Ala Gly Tyr Met Cys Ala Lys Gly Trp Arg Gly Lys
580 585 590

Thr Arg Phe Asn Pro Ser Gly Ile Lys Thr Tyr Val Arg Val Tyr Asp
595 600 605

His Asn Pro Pro Ala Asn Phe Leu Glu Gly Arg Gly Thr Leu Ser Gly
610 615 620

Ala His Val Asp Ile Met Gly Asn Phe Gln Leu Ile Glu Asp Val Ile
625 630 635 640

Lys Ile Ala Ala Gly Gly Thr Gly Glu Glu Val Gly Gly Asp Gln Val
645 650 655

Tyr Ala Gly Ile Phe Asp Trp Ser Glu Lys Ile Lys Leu Lys Leu
660 665 670

<210> SEQ ID NO 20
<211> LENGTH: 2004
<212> TYPE: DNA
<213> ORGANISM: Crepis palaestina

<400> SEQUENCE: 20
atggcggcaa ttctgaggtt ccgtaagctc tgtttcgtcg agccagcaat gaaaaactac 60
ggatcatttg aaacccagaa agacgagaaa caatcacttg acagaaagca agaaaaaagt 120
caagcaatta aagaacagga catcgataag aacaagaaga agaagcaagt aagagaatgg 180
aggtgtgtag attcttgttg ttggttcatt gggtgcatgt gtactacttg gtggctactt 240

-continued ttgtttgtat accattgttt acctgcacac ttggctggct tcaaaggccc tgaaccacct 300
ggtgtaagac tcaaaaacga agggctgacc ccacttcacc ctgtcgtttt agtccccgga 360
atcgtcaccg gcggccttga gctttgggaa ggccaacctt gttctcatgg tctttttcgt 420
aaacgccttt ggggtggtag ctttacagaa atcttagaga ggccattgtg ttggttggag 480
catttgtcac tggacaatga aacagggctc gacccgccgg ggattcgggt cagaccagtt 540
ccgggtcttg ttgcagctga ttatttcgct cctgggtatt tcgtttgggc ggttcttatc 600
gagaatctgg ctaaaatcgg gtacgaaggg aagaacatgt atatggctgc ttacgactgg 660
aggctttcgt ttcaaaacac tgaagtaagg gatcaagcac ttagcagatt gaaaatcaac 720
atcgagctaa tgtacataac caacggtaac aagaaagtag tggtggtgcc acattcaatg 780
ggggtaatct acttcctaca cttcctcaaa tgggtggaag cccctgttcc gatgggcggc 840
ggcggcggtc cagggtggtg cgacaagcat atcaaagcta tcatgaacat cggagcggcg 900
tttctcggtg ttccgaagac ggttagcggg atgctgtcgg cggaaggcaa agacgttgct 960
tttttcagag ccatggcgcc tggtttgata gattcagaaa ttctagggct ccaaactcta 1020
gaacacatga tgcgtgtagg tcgaacttgg gattctgtaa tctcattgct tcctaaaggc 1080
ggagacacca tttgggggga tttagattcc tcccctgaag atttcgaaac agaaaaccat 1140
ggtaaaatta acaacacgaa acctcagttc gtaatgaaac aggaaacgaa atacggaaga 1200
attaactcat tcggaaagac agcttccgag caacattcct caaatctcac aaatcacgat 1260
cttcaaaaag ataatttatt cgacaccggt gcaaattgcg gtgagagttg gagcgagtac 1320
ggtaaaatta gcaaggaaag cattataaaa cttgctgata acaaagcgta cacagctgga 1380
acgttaatcg atcttttacg gtttgtggca ccaaagacga tgaaacgggc cgaggcccat 1440
ttctcacatg gaatagcgga tgatcttgat gacccaaaat ataatcatta caaatattgg 1500
tcgaatccgt tagagactaa actaccagat gctccaaaca tggagatttt ttctttgtac 1560
ggggttggac tctctacaga aagatcgtat gtttatagac tgtcacaatc cgataaatgc 1620
aacagtattc cgtttagaat tgacagctca gcggagggga acggtggtcg ggggagctta 1680
cgtggcggtg tttattttgt tgatggtgat gagactgtac cggttttgag tgcggggttt 1740
atgtgtgcga aagggtggaa agggaaaact aggtttaatc cgtctgggag tgagacgtat 1800
atacgggagt ataaacataa agcaccgggg agtttgcttg agggaagggg tttggaaagt 1860
ggggctcatg ttgatatatt ggggaatgtg gcattgattg aggatgtttt gagggtggcg 1920
gccggagctt ctggggtgga gattggcggt gatcggattt attcagatat attgaagatg 1980
gcggatagag taaatattaa actt 2004

<210> SEQ ID NO 21
<211> LENGTH: 668
<212> TYPE: PRT
<213> ORGANISM: crepis palaestina

<400> SEQUENCE: 21

Met Ala Ala Ile Leu Arg Phe Arg Lys Leu Cys Phe Val Glu Pro Ala
1 5 10 15

Met Lys Asn Tyr Gly Ser Phe Glu Thr Gln Lys Asp Glu Lys Gln Ser
20 25 30

Leu Asp Arg Lys Gln Glu Lys Ser Gln Ala Ile Lys Glu Gln Asp Ile
35 40 45

Asp Lys Asn Lys Lys Lys Lys Gln Val Arg Glu Trp Arg Cys Val Asp

-continued

```
    50                  55                  60

Ser Cys Cys Trp Phe Ile Gly Cys Met Cys Thr Thr Trp Trp Leu Leu
65                  70                  75                  80

Leu Phe Val Tyr His Cys Leu Pro Ala His Leu Ala Gly Phe Lys Gly
                85                  90                  95

Pro Glu Pro Pro Gly Val Arg Leu Lys Asn Glu Gly Leu Thr Pro Leu
            100                 105                 110

His Pro Val Val Leu Val Pro Gly Ile Val Thr Gly Gly Leu Glu Leu
        115                 120                 125

Trp Glu Gly Gln Pro Cys Ser His Gly Leu Phe Arg Lys Arg Leu Trp
    130                 135                 140

Gly Gly Ser Phe Thr Glu Ile Leu Glu Arg Pro Leu Cys Trp Leu Glu
145                 150                 155                 160

His Leu Ser Leu Asp Asn Glu Thr Gly Leu Asp Pro Pro Gly Ile Arg
                165                 170                 175

Val Arg Pro Val Pro Gly Leu Val Ala Ala Asp Tyr Phe Ala Pro Gly
            180                 185                 190

Tyr Phe Val Trp Ala Val Leu Ile Glu Asn Leu Ala Lys Ile Gly Tyr
        195                 200                 205

Glu Gly Lys Asn Met Tyr Met Ala Ala Tyr Asp Trp Arg Leu Ser Phe
    210                 215                 220

Gln Asn Thr Glu Val Arg Asp Gln Ala Leu Ser Arg Leu Lys Ile Asn
225                 230                 235                 240

Ile Glu Leu Met Tyr Ile Thr Asn Gly Asn Lys Lys Val Val Val Val
                245                 250                 255

Pro His Ser Met Gly Val Ile Tyr Phe Leu His Phe Leu Lys Trp Val
            260                 265                 270

Glu Ala Pro Val Pro Met Gly Gly Gly Gly Gly Pro Gly Trp Cys Asp
        275                 280                 285

Lys His Ile Lys Ala Ile Met Asn Ile Gly Ala Ala Phe Leu Gly Val
    290                 295                 300

Pro Lys Thr Val Ser Gly Met Leu Ser Ala Glu Gly Lys Asp Val Ala
305                 310                 315                 320

Phe Phe Arg Ala Met Ala Pro Gly Leu Ile Asp Ser Glu Ile Leu Gly
                325                 330                 335

Leu Gln Thr Leu Glu His Met Met Arg Val Gly Arg Thr Trp Asp Ser
            340                 345                 350

Val Ile Ser Leu Leu Pro Lys Gly Gly Asp Thr Ile Trp Gly Asp Leu
        355                 360                 365

Asp Ser Ser Pro Glu Asp Phe Glu Thr Glu Asn His Gly Lys Ile Asn
    370                 375                 380

Asn Thr Lys Pro Gln Phe Val Met Lys Gln Glu Thr Lys Tyr Gly Arg
385                 390                 395                 400

Ile Asn Ser Phe Gly Lys Thr Ala Ser Glu Gln His Ser Ser Asn Leu
                405                 410                 415

Thr Asn His Asp Leu Gln Lys Asp Asn Leu Phe Asp Thr Gly Ala Asn
            420                 425                 430

Cys Gly Glu Ser Trp Ser Glu Tyr Gly Lys Ile Ser Lys Glu Ser Ile
        435                 440                 445

Ile Lys Leu Ala Asp Asn Lys Ala Tyr Thr Ala Gly Thr Leu Ile Asp
    450                 455                 460

Leu Leu Arg Phe Val Ala Pro Lys Thr Met Lys Arg Ala Glu Ala His
465                 470                 475                 480
```

-continued

```
Phe Ser His Gly Ile Ala Asp Asp Leu Asp Asp Pro Lys Tyr Asn His
                485                 490                 495

Tyr Lys Tyr Trp Ser Asn Pro Leu Glu Thr Lys Leu Pro Asp Ala Pro
            500                 505                 510

Asn Met Glu Ile Phe Ser Leu Tyr Gly Val Gly Leu Ser Thr Glu Arg
        515                 520                 525

Ser Tyr Val Tyr Arg Leu Ser Gln Ser Asp Lys Cys Asn Ser Ile Pro
    530                 535                 540

Phe Arg Ile Asp Ser Ser Ala Glu Gly Asn Gly Gly Arg Gly Ser Leu
545                 550                 555                 560

Arg Gly Gly Val Tyr Phe Val Asp Gly Asp Glu Thr Val Pro Val Leu
                565                 570                 575

Ser Ala Gly Phe Met Cys Ala Lys Gly Trp Lys Gly Lys Thr Arg Phe
            580                 585                 590

Asn Pro Ser Gly Ser Glu Thr Tyr Ile Arg Glu Tyr Lys His Lys Ala
        595                 600                 605

Pro Gly Ser Leu Leu Glu Gly Arg Gly Leu Glu Ser Gly Ala His Val
    610                 615                 620

Asp Ile Leu Gly Asn Val Ala Leu Ile Glu Asp Val Leu Arg Val Ala
625                 630                 635                 640

Ala Gly Ala Ser Gly Val Glu Ile Gly Gly Asp Arg Ile Tyr Ser Asp
                645                 650                 655

Ile Leu Lys Met Ala Asp Arg Val Asn Ile Lys Leu
            660                 665

35
35
```